United States Patent [19]

Kok et al.

[11] Patent Number: 5,683,909
[45] Date of Patent: Nov. 4, 1997

[54] **PLASMIDS REPLICATABLE IN *BACILLUS SUBTILIS, E. COLI* AND LACTIC ACID STREPTOCOCCUS BACTERIA**

[75] Inventors: Jan Kok, Groningen; Jan Maat, Monster; Josephus Mauritius van der Vossen, Groningen; Gerard Venema, Haren, all of Netherlands

[73] Assignee: Van Den Bergh Foods Company, Division of Conopco, Inc.

[21] Appl. No.: 135,133

[22] Filed: Oct. 12, 1993

Related U.S. Application Data

[63] Continuation of Ser. No. 533,997, Jun. 4, 1990, abandoned, which is a continuation of Ser. No. 346,375, Apr. 28, 1989, abandoned, which is a continuation of Ser. No. 776,171, Sep. 11, 1985, abandoned.

[30] Foreign Application Priority Data

Mar. 2, 1984 [NL] Netherlands ............................ 8400687

[51] Int. Cl.$^6$ ............................ C12N 15/69; C12N 15/70; C12N 15/74; C12N 15/75
[52] U.S. Cl. ..................... 435/172.3; 435/69.1; 435/183; 435/220; 435/252.3; 435/252.31; 435/252.33; 435/253.4; 435/320.1; 536/23.1; 536/23.2; 536/23.7
[58] Field of Search .................................. 435/69.1, 183, 435/220, 252.3, 252.33, 252.31, 320.1, 172.3, 253.4; 536/23.1, 23.2, 23.7

[56] References Cited

U.S. PATENT DOCUMENTS

| | | | |
|---|---|---|---|
| 4,532,211 | 7/1985 | Sako et al. | 435/172.3 |
| 4,649,119 | 3/1987 | Sinskey et al. | 435/317 |

FOREIGN PATENT DOCUMENTS

| | | |
|---|---|---|
| 68740 | 1/1983 | European Pat. Off. . |

OTHER PUBLICATIONS

Moir et al. Gene 19:127 (1982).
Sanders, Dissertation Thesis, 1983 NCSU, Raleigh voided as CA 103(7):48899x.
Boyd "Microbiology" pp. 82–83, Mosby College Pub., St. Louis, MO, 1984.
Otto, R., W.M. deVos, and J. Gavrieli. 1982. Plasmid DNA in *Streptococcus cremoris* Wg2: Influence of pH on Selection in chemostats of a variant lacking a protease plasmid. Appln. Enfiron. Microbial. 43:1272–1277.
Wouters, J.T.M., and J. Stadhouders. 1982. Genetica van melkzuurbacterien; een weg tot nieuwe toepassingen? Voedingsmiddelentechnologie 15::(No. 24) 19–21 and (No. 26) 26–28 English Summary on p. 19 only.
Horinouchi, S., and B. Weisblum. 1982. Nucleotide sequence and functional map of pC194, a plasmid that specifies inducible chloramphenicol resistance. J. Bacterial. 150:815–825.

Horinouchi, S., and B. Weisblum. 1982. Nucleotide sequence and functional map of pE194, a plasmid that specifies inducible resistance to macrolide, linosamide, and streptogramin type B antibiotics. J.Bacteriol. 150:804–814.
Vosman, B., and G. Venema. 1983. Introduction of a *Streptococcus cremoris* plasmid in *Bacillus subtilis*. J. Bacteriol. 156:920–921.
Lacey, R.W., and I. Chopra. 1974. Genetic studies of a multi–resistant strain of *Staphylococcus aureus*. J. Med. Microbiol. 7:285–297.
Horinouchi, S., and B. Weisblum. 1980. Post–transcriptional midification of mRNA conformation: mechanism that regulates erytnromycin–induced resistance. Proc. Natl. Acad. Sci. USA 77:7079–7083.
Gasson, M.J. 1983. Plasmid complements of *Streptococcus lactis* NC00712 and other lactic streptococci after protoplast–induced curing. J. Bacteriol. 154:1–9.
Williams, D.M., E.J. Duvall and P.S. Lovett. 1981. Cloning restriction fragments that promote expression of a gene in *Bacillus subtilis*. J. Bacteriol. 146:1162–1165.
Bron, S., and G. Venema. 1972. Ultraviolet inactivation and excision–repair in *Bacillus subtilis*. I. Construction of a transformable eight–fold auxotrophic strain and two ultraviolet–sensitive derivatives. Mutat.Res. 15:1–10.
Weisblum, B., M.Y. Graham, and D. Dubnau. 1979. Plasmid copy number control: isolation and characterization of high–copy–number mutants of plasmid pE194. J. Bacteriol. 137:635–643.
Hohn, B. 1979. In vitro packaging of lambda and cosmid DNA. Methods in Enzymol. 68:299–309.
Rotttander, E., and T. A. Trautner. 1970. Genetic and transfection studies with *Bacillus subtilis* phage SP50. Mol. Gen. Genet. 108:47–60.
Terzaghi, B.E., and W.E. Sandine. 1975. Improved medium for lactic streptococci and their bacteriophages. Appln. Microbiol. 29:807–813.
deVos, W.M., G. Venema, U. Canosi, and T.A. Trautner. 1981. Plasmid transformation in *Bacillus subtilis:* fate of plasmid DNA. Mol. Genet. 181:424–433.
Ish–Horowicz, D., and J.F. Burke. 1981. Rapid and efficient cosmid cloning. Nucleic Acids Res. 9:2989–2999.
Chang, S., and S.N. Cohen. 1979. High frequency transformation of *Bacillus subtilis* protoplasts by plasmid DNA. Mol. Gen. Genet. 168:111–115.
Mandel, M., and A. Higa. 1970. Calcium–dependent bacteriophage DNA infection. J. Mol. Biol. 53:159–162.

(List continued on next page.)

*Primary Examiner*—John Leguyader
*Attorney, Agent, or Firm*—Cushman Darby & Cushman IP Group of Pillsbury Madison & Sutro, LLP

[57] ABSTRACT

The claimed invention is drawn to a recombinant plasmid which can replicate in *Bacillus subtilis, Escherichia coli*, and lactic acid Streptococcus bacteria comprising the replication of origin from *Streptococcus cremoris* plasmid pWV01 as its origin of replication, in addition to coding marker genes and genes of interest which code for improved fermenting properties.

10 Claims, 9 Drawing Sheets

OTHER PUBLICATIONS

Kondo, J.K., and L.L. McKay. 1982. Transformation of *Streptococcus lactis* protoplasts by plasmid DNA. Appl. Environ. Microbiol. 43:1213–1215.

Spigizen, J. 1958. Transformation of biochemically deficient strains of *Bacillus subtilis* by deoxynucleate. Proc. Natl. Acad. Sci. USA 44:1072–1078.

Scheer–Abramowitz, J., F.J. Gryczan, and D. Dabnau. 1981. Origin and mode of replication of plasmids pE194 and pUB110. Plasmid 6:67–77.

Southern, E.M. 1975. Detection of specific sequences among DNA fragments separated by gel electrophoresis. J. Mol. Biol. 98:503–517.

Barany, F., J.D. Boeke, and A. Tomasz. 1982. Staphylococcal plasmids that replicate and express erythromycin resistance in both *Streptococcus pneumoniae* and *Escherichia coli* Proc. Natl. Acad. U.S.A. 79:2991–2995.

Goze, A., and S.D. Ehrlich. 1980. Replication of plasmids from *Staphyloccus aureus* in *Escherichia coli.* Proc. Natl. Acad. Sci. U.S.A. 77:7333–7337.

Jarvis, A.W., and B.D.W. Jarvis. 1981. Deoxyribonucleic acid homology among lactic streptococci. Appln. Environ. Microbiol. 41:77–83.

Klotz, L.C., and B.H. Zimm. 1972. Size of DNA by viscoelastic measurements: results on bacteriophages. *Bacillus subtillis* and *Escherichia coli.* J. Mol. Biol. 72:779–800.

Ostroff, G.R., and J.J. Pene. 1983. Molecular cloning with bifunctional plasmid vectors in *B. subtillis:* Isolation of a spontaneous mutant of *B. subtillis* with enlarged transformability for *E. coli–propagated* chimeric plasmid DNA. J. Bacteriol. 156:934–936.

Exterkate, F.A. 1975. An introductory study of the proteolytic system of *S. cremoris* strain HP. Neth. Milk Dairy J. 29:303–318.

Covarrubias, L., and F. Bolivar. 1982. Construction and characterisation of new cloning vehicles VI. Plasmid pBR329, a new derivative of pBR328 lacking the 482–base––pair inverted duplication. Gene 17:79–89.

Chang, A.C.Y., and S.N. Cohen. 1978. Construction and characterization of amplifiable multicopy DNA cloning vehicles derived from the P15A cryptic miniplasmid. J. Bacteriol. 134:1141–1156.

Limsowtin, G.K.Y., and B.E. Terzaghi. 1976. Agar medium for the differentiation of "fast and slow" coagulating cells in lactic streptococcal cultures. N.Z.J. Dairy Sci. Technol. 11:65–66.

Brown, J. Howard and Howe, Paul E., 1922. Transparent Milk as a Bacteriological Medium. J. Bacteriol. 7:511–514.

LeBlanc, D.J., and L.N. Lee. 1979. Rapid screening procedure for detection of plasmids in streptococci. J. Bacteriol. 140:1112–1115.

Blin, N., A.V. Gabain, and H. Bujard. 1975. Isolation of large molecular weight DNA from agarose gels for further digestion by restriction enzymes. FEBS Lett. 53:84–86.

Okamoto, T., Y. Fujita, and R. Irie. 1983. Protoplast formation and regeneration of *S. lactis* cells. Agric. Biol. Chem. 47:259–263.

Bradford, M.M. 1976. A rapid and sensitive method for the quantitation of microgram quantities of protein utilizing the principle of protein–dye binding. Anal. Biochem. 72:248–254.

Elferink, M.G., K.J. Hellingwerf, P.A. Michels, H.G. Seyen, and W.N. Konings. 1979. Immunochemical analysis of membrane vesicles and chromatophores of *Rhodopseudomonas sphaeroides* by crossed immunoelectrophoresis. FEBS Lett. 107:300–307.

Norrander, J., T. Kempe, and J. Messing. 1983. Construction of improved M13 vectors using oligodeoxynucleotide–directed mutagenesis. Gene 26:101–106.

Towbin, H., T. Staehlin and J. Gordon, 1979. Electrophoretic transfer of proteins from polyacrylamide gels to nitrocellulose sheets: Procedure and some applications. Proc. Nat. Acad. Sci. U.S.A. 76, 4350–4354.

Exterkate, F.A. 1976. Comparison of strains of *S. cremoris* for proteolytic activities associated with the cell wall. Neth. Milk Dairy J. 30:95–105.

Larsen, L.D., and L.L. McKay. 1978. Isolation and characterisation of plasmid DNA in *S. cremoris.* Appln. Environ. Microbiol. 36:944–952.

Rigby, P.W.J., M.M. Dieckmann, C. Rhodes, and P. Berg. 1977. Labeling of DNA to high specific activity in vitro by nick translation with DNA polymerase I. J. Mol. Biol. 113:237–251.

Chemical Abstracts, vol. 98, No. 21, 23 May 1983 (Columbus, Ohio, U.S.) V. I. Golubkov et al.: "New Class of cryptic plasmids of Streptococcus group A and their use as vector riplicons", see p. 185, abstract No. 173950m & Mol. Biol. (Moscow) 1983, 17(1)136–42 (Russ).

Chemical Abstracts, vol. 97, No. 15, Oct. 1982 (Columbus, Ohio, U.S.), see p. 163, abstract No. 121358j, and JP, A, 8286299 (Daiichi Seiyaku Co. Ltd.) 29 May 1982.

Agricultural and Biological Chemistry, vol. 46, No. 2, Feb. 1982, M. Kono et al.: "In vivo construction of chloramphenicol resistant plasmid pTP62 in *Bacillus subtilis* by transformation of *Streptococcus faecalis* Plasmid", See pp. 569, 570.

Chemical Abstracts, vol. 102, No. 1, 7 Jan. 1985 (Columbus, Ohio, U.S.) J. Kok et al.: "Construction of plasmid cloning vectors for lactic streptococci which also replicate in *Bacillus subtilis* and *Escherichia coli"* see p. 121, abstract No. 1181w, & Appl. Environ. Microbiol. 1984, 48(4), 726–31.

Construction pf pGK3 and pGKV1 and pGKV2

Fig. 5A    Fig. 5B
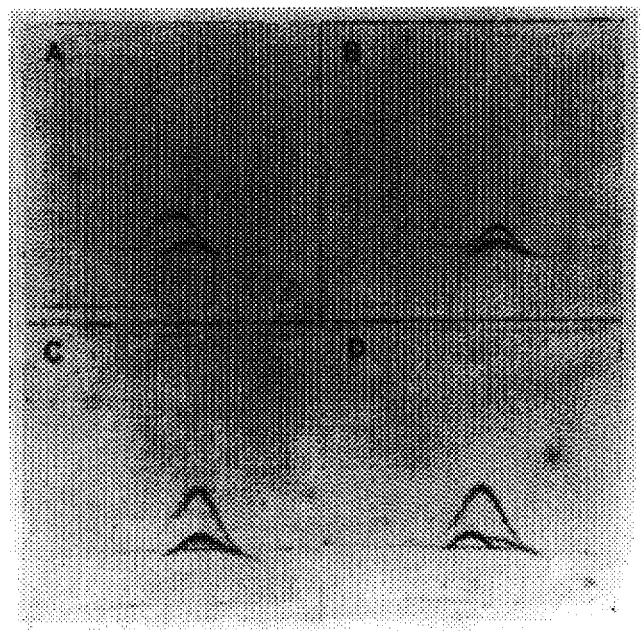
Fig. 5C    Fig. 5D
Fig. 6A    Fig. 6B

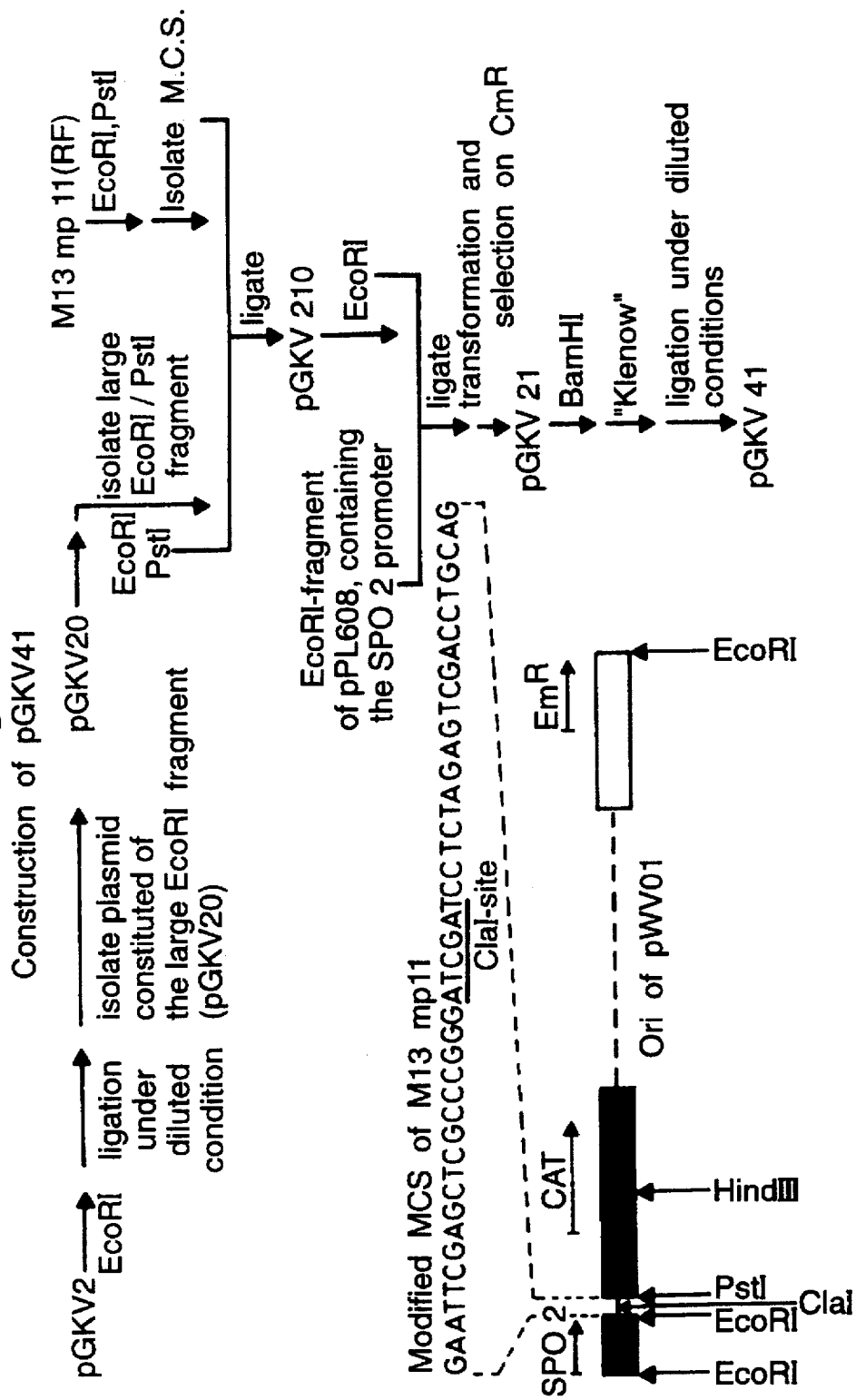

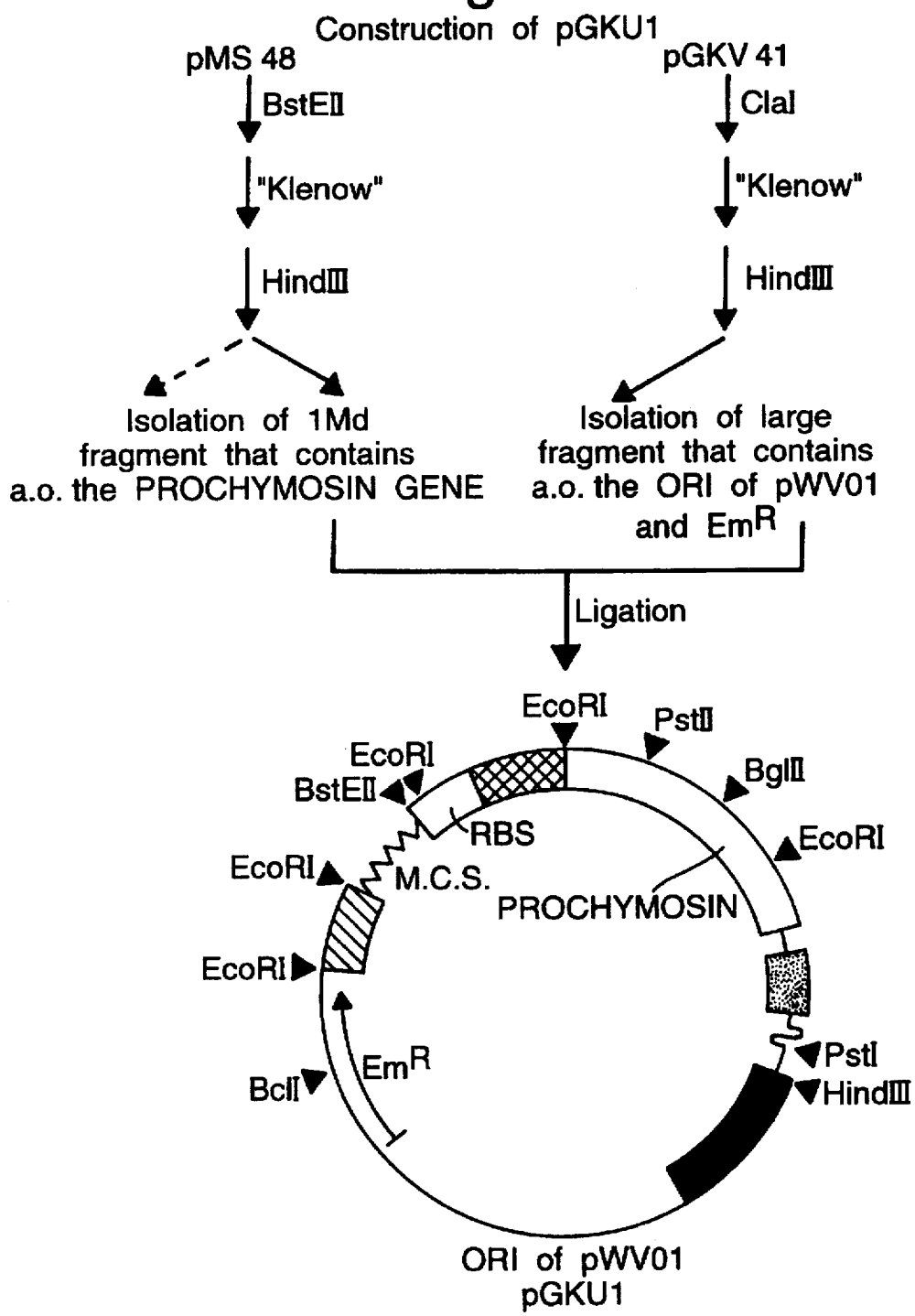

PLASMIDS REPLICATABLE IN *BACILLUS SUBTILIS*, *E. COLI* AND LACTIC ACID STREPTOCOCCUS BACTERIA

This is a continuation of application Ser. No. 07/533,997, filed on Jun. 4, 1990, which was abandoned upon the filing hereof which is a continuation of Ser. No. 07/346,375, filed Apr. 28, 1989, now abandoned, which is a continuation of Ser. No. 06/776,171, filed Sep. 11, 1985, now abandoned.

BACKGROUND OF THE INVENTION

The invention relates to recombinant plasmids, bacteria containing such recombinant plasmids and processes for preparing food products, animal feedstuffs or ingredients thereof or proteins such as enzymes using such bacteria. More specifically, the invention relates to recombinant plasmids capable of replicating in *Bacillus subtilis*, *Escherichia coli* and lactic acid bacteria. Such recombinant plasmids are highly desirable if they contain at least one homologous or heterologous gene that can be brought to expression in a selected host cell, thereby improving or enlarging the fermentative properties of the host cell.

Most recombinant DNA work has been carried out with bacteria such as *E. coli* and *B. subtilis*, but relatively little is known on the genetics of streptococci which belong to the lactic acid bacteria. The streptococci are, however, of much more commercial importance to the food industries, for example for the preparation of dairy products by fermentation of milk and milk products and for the preparation of other fermented foods such as meat, soured bread and fermented vegetables, as well as animal feedstuffs.

High-quality starter cultures of lactic streptococci used in the dairy industry for the production of cheese, yoghurt and the like have to be controlled carefully for their strain characteristics such as acid production, proteolytic activity, phage resistance and flavour formation, since it can easily occur that mutants are formed or they become infected, whereby the quality of the starter cultures is destroyed (see reference 1). Some thoughts on what might be done to improve lactic acid cultures by means of recombinant DNA technology were published by Wouters and Stadhouders (see reference 2), but these authors do not give practical solutions.

Thus a need exists for recombinant plasmids which can express proteins in lactic acid bacteria, so that these transformed lactic acid bacteria have improved or new properties which are desirable in the food industries.

BRIEF SUMMARY OF THE INVENTION

The present invention provides recombinant plasmids capable of replication in *Bacillus subtilis*, *Escherichia coli* and lactic acid bacteria, in particular streptococci, containing DNA from at least one plasmid occurring in lactic acid bacteria, at least one marker being capable of expression in the three types of microorganisms and at least one piece of insert-DNA which, when expressed, gives the microorganism an improved or new property.

Preferably such plasmids contain at least part of the *Streptococcus cremoris* plasmid pWV01, in particular the largest ClaI fragment of plasmid pWV01. The genes for chloramphenicol resistance ($Cm^R$) and erythromycin resistance ($Em^R$) originating from *Staphylococcus aureus* plasmids pC194 and pE194 cop-6, respectively, proved to be suitable markers. But auxotrophic markers, such as the genes involved in the lactose metabolism are preferred to the above-mentioned antibiotic resistance markers, since maintenance of a selection pressure with antibiotics during the preparation of fermented foods is highly undesirable. Examples of pieces of insert-DNA which can give the bacteria the desirable properties are structural genes such as genes encoding proteases able to split proteins into peptides and/or amino acids which the bacteria can assimilate, genes encoding milk-clotting enzymes such as chymosin, genes giving bacteriophage resistance to the bacteria, genes which influence the citrate metabolism, and genes involved in the lactose metabolism.

The invention further provides recombinant vector plasmids which are suitable as starting material for the preparation of the above-mentioned recombinant plasmids by insertion of structural genes, which structural genes, when expressed, will give the bacterium the desirable properties.

The plasmids should also contain regulatory sequences, e.g. a promoter attached to and belonging to the structural gene, or a (strong) promoter already present in the vector plasmid which may be either a homologous or a heterologous promoter and optionally transcription termination sequences.

The invention also provides bacteria, in particular streptococci, containing such recombinant plasmids with or without the inserted structural genes.

Another embodiment of the invention relates to a process for preparing fermented food products, animal feedstuffs or ingredients thereof, in which process the above-described transformed bacteria are used in the fermentation, as well as to the products prepared by such a process.

Finally the invention relates to a process for the preparation of proteins which are normally not made by lactic acid bacteria or only in small amounts, as well as to the proteins so obtained.

BRIEF DESCRIPTION OF THE DRAWINGS

The specification contains the following drawings which help to explain the invention.

FIG. 3 shows that pGD4 and pGD6 together comprise HindIII fragment C of pWV05.

In FIG. 5 crossed and tandem crossed immunoelectrophoresis of cell-free extracts of *B. subtilis* PDL1

(pGKV500), see (A) and (C), respectively, and of purified proteolytic systems of *S. cremoris* Wg2, see (B) and (D), respectively, are given, using antibodies raised against the proteolytic system of *S. cremoris* Wg2.

In FIG. 6 crossed immunoelectrophoresis of cell-free extracts of *S. lactis* MG1363 (pGKV2), see (A), and *S. lactis* MG1363 (pGKV500), see (B), are given, using antibodies raised against the proteolytic system of *S. cremoris* Wg2.

In FIG. 7 the construction of pGKV41 from pGKV2 and M13 mp11 is given, as well as a modified Multiple Cloning Site (MCS) derived from M13 mp11 and the linear restriction enzyme map of pGKV41. This plasmid has an MCS between the SPO2 promoter from *B. subtills* and the CAT gene from *B. pumilis*.

In FIG. 8 the construction of pGKU1 is given. This is a derivative of pGKV41 also containing a chemically synthesized Ribosome Binding Site (RBS), a chemically synthesized alpha-amylase signal sequence and the methionyl-prochymosin gene derived from pMS 48.

Figures 9A, 9B:
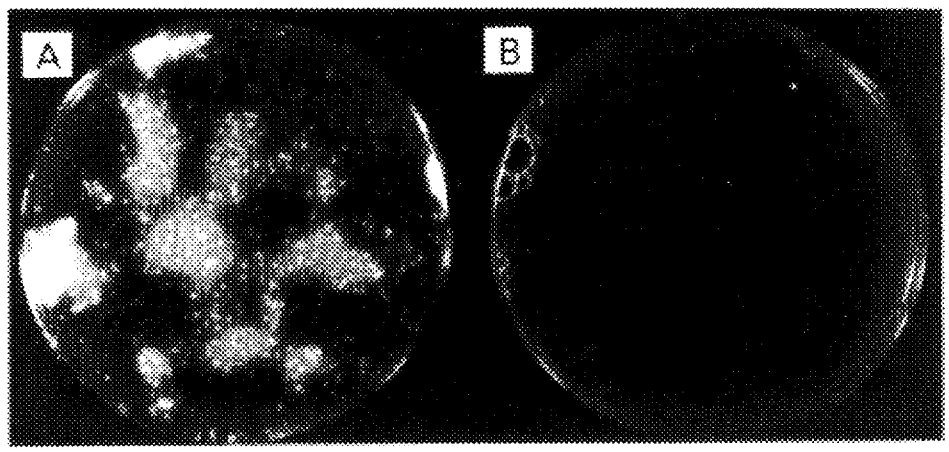

In FIG. 9 the results of growth of *S. lactis* MG1363 (pGKV500), see (A), and *S. lactis* MG1363 (pGKV2), see (B), on transparent citrate-milk-agar plates containing glucose and erythromycin are given, which deviate as a consequence of their metabolic differences.

Figure 10:
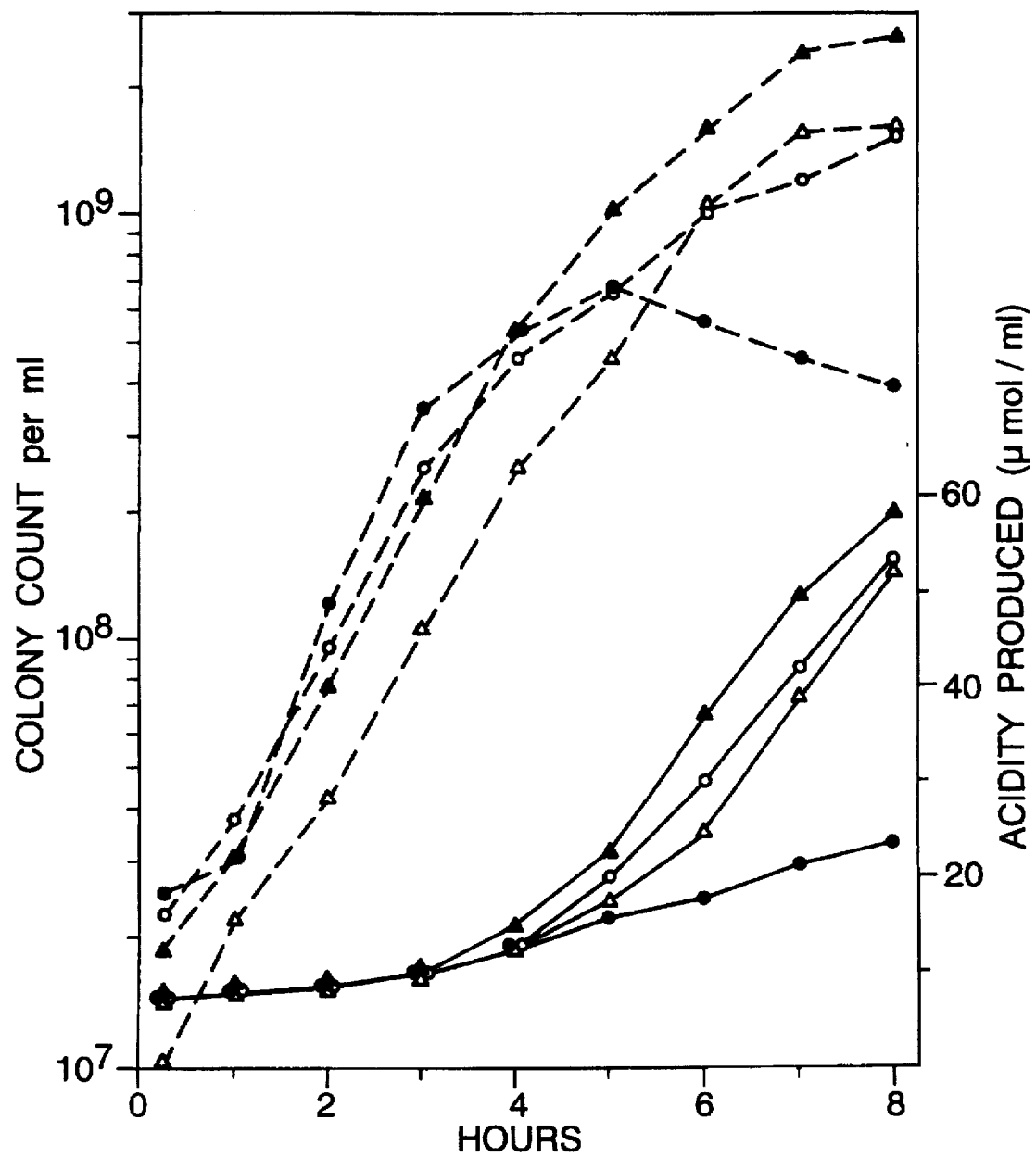

In FIG. 10 the effect of pGKV500 on *S. lactis* MG 1363 growth and acid production in milk is shown compared with the effect of pGKV2 and two wild type strains, i.e. *S. cremoris* Wg2 (Prt$^+$) and *S. lactis* 712.

DETAILED DESCRIPTION

As mentioned above, a need exists for recombinant plasmids which can express proteins in lactic acid bacteria so that these transformed lactic acid bacteria have improved or new properties which are desirable in the food industries.

The present invention now provides recombinant plasmids containing genes which can be expressed not only in *B. subtilis* or *E. coli* but also in lactic acid bacteria, in particular streptococci. As a consequence the lactic acid bacteria thus transformed can be used for the fermentative preparation of human foodstuffs, animal feedstuffs and ingredients for both, whereby these bacteria have improved or novel properties.

Thus a first aspect of the invention is a recombinant plasmid capable of replication in *Bacillus subtills*, *Escherichia coli* and lactic acid bacteria, constructed from a plasmid occurring in lactic acid bacteria, into which both at least one marker and at least one piece of insert-DNA have been inserted, which marker is capable of expression in the three types of microorganisms referred to, and which piece of insert-DNA, when expressed, gives the microorganism an improved or new property.

Preferably the recombinant plasmid according to the invention contains at least two markers capable of expression in the three types of microorganisms referred to.

It is further preferred that at least one marker is capable of being inactivated by the insertion of insert-DNA, having the advantage that the piece of insert-DNA can be inserted in the marker. Very suitable markers appeared to be the chloramphenical resistance (Cm$^R$) gene and the erythromycin resistance (Em$^R$) gene originating from the *Staphylococcus aureus* plasmids pC194 (see reference 3) and pE194 cop-6, respectively (see reference 4). One advantage of these markers is that their complete base sequence is known. A further advantage inherent in the Em$^R$ marker is the fact that the Em$^R$ promoter is inducible, so that the expression of a gene brought under the regulation of the promoter of the Em$^R$ gene is also inducible in the lactic acid bacteria. Another advantage of the Em$^R$ gene is that it contains a unique BclI site which makes insertion easier (see the description of pGk12 below).

It was known that the Cm$^R$ and Em$^R$ genes were capable of expression in *B. subtilis* and *E. coli*. It has now been found that these genes surprisingly are capable of expression in lactic acid bacteria. The recombinant plasmids according to the invention preferably contain at least part of the *Streptococcus cremoris* plasmid pWV01 (see references 1 and 5).

As a starting material for the preparation of the above-described expression plasmids a recombinant vector plasmid can be used that is also capable of replication in *B. subtilis*, *E. coli* and lactic acid bacteria, in particular streptococci, and that contains at least one marker which is capable of expression in the three types of microorganisms referred to and/or contains at least part of the *Streptococcus cremoris* plasmid pWV01, which part carries the replication origin for expression in *Streptococcus cremoris*.

An example of the first generation of vector plasmids, i.e. those containing one marker, is one designated as pGK1, which was prepared by inserting a MboI fragment from pGL112, which is a chimera of plasmids pC194 and pUB110 (see reference 6), into the MboI site of pWV01 (see FIG. 1). pGK1 has a unique HpaII site resulting from the plasmid pC194 starting at nucleotide 973 on the sequence of Horinouchi and Weisblum (see reference 3) and contains the entire Cm$^R$ gene.

This plasmid was then converted into a smaller plasmid, designated as pGK11, by treatment with ClaI followed by religation in order to remove the small fragment between the two ClaI sites. In transformation studies, it was found that this small fragment could be deleted without any influence on the essential characteristics of plasmids pGK1 and pGK11. But the advantage is that pGK11, in addition to the HpaII site, has another unique restriction site, namely ClaI.

An example of the second generation of vector plasmids containing selection markers was made by incorporation of the Em$^R$ gene from pE194 cop-6 into pGK11 by treating pE194 cop-6 with ClaI and HpaII and ligating the largest fragment containing the Em$^R$ gene with the Cla-treated pGK11. One of the resulting plasmids had the composition as given in FIG. 1 and was designated as pGK12. This plasmid has three unique restriction sites for BclI, ClaI and HpaII.

The BclI site is located within the Em$^R$ gene, and insertion of DNA in this site inactivates the gene (see reference 7). Therefore, pGK12 can be used for cloning by insertional inactivation of fragments produced by BamHI, BclI, BglII and MboI (which all have (5')GATC(3') protruding ends) by first selecting for Cm$^R$ transformants. pGK12 also offers the possibility of directional cloning with Em$^R$ inactivation: cleavage of the plasmid with BclI and ClaI results in a vector with different protruding ends.

The ClaI and HpaII sites are located outside both resistance genes and can be used for insertions of foreign DNA fragments generated by ClaI, HpaII and TaqI, which all have (5')CG(3') protruding ends. Insertion with inactivation of Cm$^R$ is also possible by removing the ClaI-HpaII fragment containing the Cm$^R$ gene of pGK12 and insertion of a fragment having protruding ends generated by ClaI, HpaII, TaqI or combinations thereof.

Although these antibiotic-resistant markers appeared very helpful in cloning foreign genes into lactic acid bacteria, it is preferred to inactivate or even delete these markers and to use auxotrophic markers, which are advantageous for microorganisms used in the food industry. Moreover, they can give advantages to the host cell in the fermentation process. Examples of such an auxotrophic marker are the genes for lactose metabolism (see reference 8), which can be integrated in the BclI site of pGK12.

Another example of the first generation of vector plasmids is one designated as pGK3, which was made by treating the *Streptococcus cremoris* Wg2 plasmid pWV01 with ClaI, isolating the largest ClaI fragment and ligating same with the largest ClaI-HpaII fragment of pE194 cop-6, which contains the $Em^R$ gene.

This pGK3 was converted to a plasmid of the second generation by (1) linearizing this plasmid with ClaI and filling in the cohesive ends by the Klenow fragment of *E. coli* DNA polymerase I to obtain a first DNA molecule;

(2) subjecting the *Bacillus subtilis* vector pPL608 (see reference 9) to complete digestion with PvuII and partial digestion with EcoRI, isolating the largest PvuII-EcoRI fragment containing the SPO2 promoter and the CAT gene, and filling in the EcoRI cohesive end by the Klenow fragment of *E. coli* DNA polymerase I to obtain a second DNA molecule; and (3) ligating the first and second DNA molecules.

Figure 2:
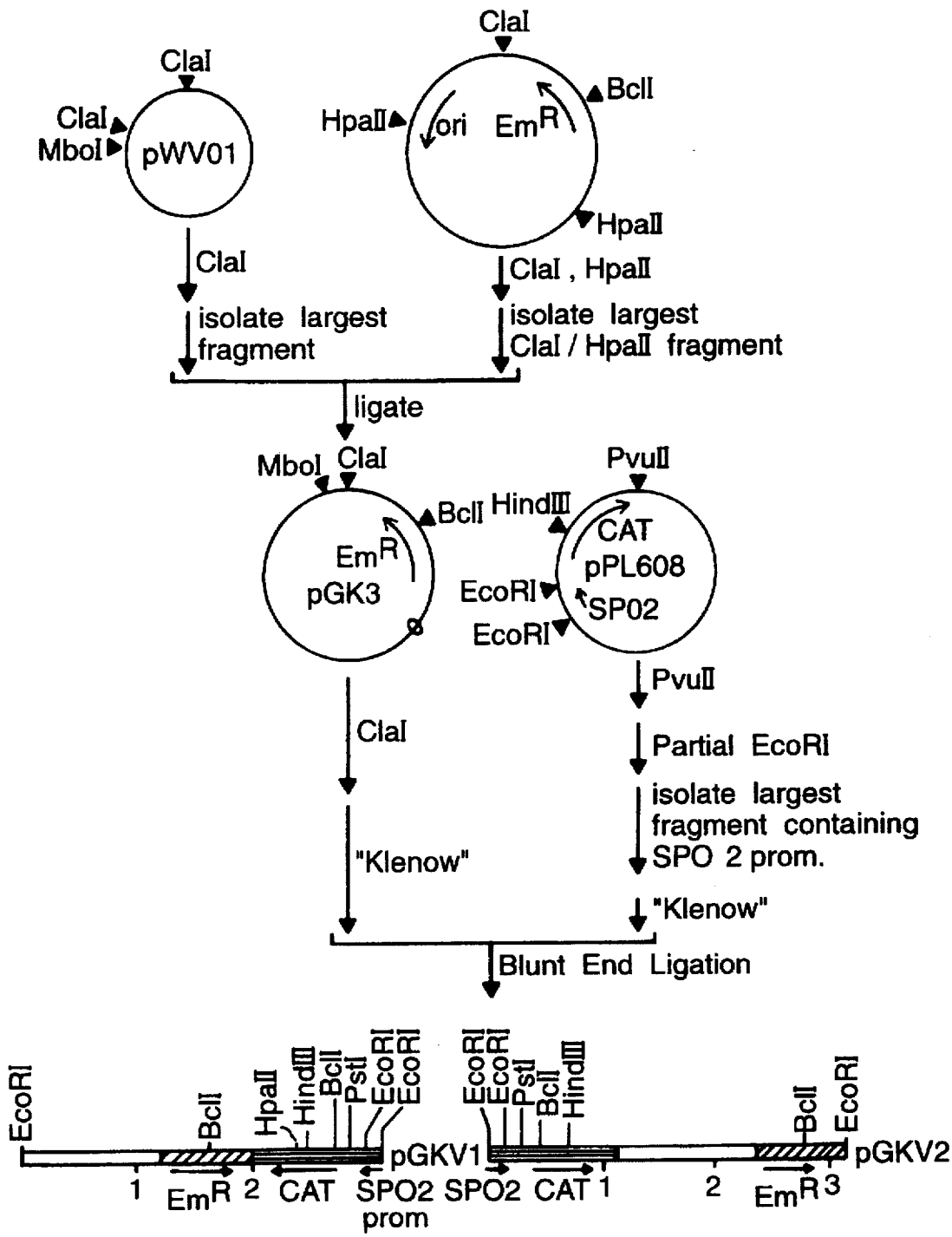
In FIG. 2 linear restriction enzyme maps of plasmids pGKV1 and pGKV2 are given and important genes and their orientation are indicated, as well as their preparation from pPL608 and pGK3 and the preparation of pGK3 from pWV01 and pE194 cop-6. All three plasmids contain a BclII site in the $Em^R$ gene; moreover pGKV1 and pGKV2 contain a unique HindIII site in the CAT gene.

The resulting plasmids occurred in two forms which were designated as pGKV1 and pGKV2. Their preparation and linear restriction enzyme maps are given in FIG. 2.

pGKV1 and pGKV2 both contain a unique HindIII site in the CAT gene under control of the *B. subtilis* SPO2 promoter as shown in FIG. 2. CAT stands for chloramphenicol acetyl transferase, which enzyme inactivates chloramphenicol by converting it successively to the inactive 3-acetyl and 1,3-diacetyl derivatives (see reference 3). Thus, although the CAT gene is different from the $Cm^R$ gene, they both give $Cm^R$ transformants when expressed.

Plasmid pGKV2 was used to prepare a recombinant plasmid containing a structural gene coding for a protease, which plasmid was designated as pGKV500. It was made by inserting the 4.3 Md HindIII fragment C of the *Streptococcus cremoris* Wg2 plasmid pWV05, which preparation is described later in this specification, into the unique HindIII site of plasmid pGKV2.

As a consequence of the insertion in the HindIII site of the CAT gene, transformation with pGKV500 gives $Cm^S Em^R$ transformants in which S stands for sensitive.

When recombinant plasmids are made which express the structural genes in lactic acid bacteria, it is desirable for practical application to remove at least one marker, provided that the plasmids are stable enough to replicate without a selection pressure, in order to make the transformed microorganisms again sensitive to antibiotics.

If an auxotrophic marker is present in the recombinant plasmids according to the invention, they can give to the bacteria in which these plasmids are expressed an advantage over other bacteria, in that the transformed bacteria can use the ingredients of the fermentation medium more efficiently and therefore can grow better.

Another embodiment of the invention relates to *Bacillus subtilis* bacteria, *Escherichia coli* bacteria and lactic acid bacteria, in particular streptococci, provided with one or more recombinant plasmids according to the invention, either with or without a piece of insert-DNA coding for improved new properties.

A preferred lactic acid bacterium is one provided with a more stable and/or higher protease activity as a result of the insert DNA in the plasmid coding for the protease.

Another preferred lactic acid bacterium is one having a reduced bacteriophage sensitivity as a result of the insert-DNA in the plasmid containing one or more genes for bacteriophage resistance.

Still another preference relates to a lactic acid bacterium capable of producing a milk-clotting enzyme or a precursor thereof, which precursor forms the enzyme during fermentation of a milk product, more particularly one which is capable of producing chymosin or one of its precursors, such as (methionyl-)pseudochymosin, (methionyl-)prochymosin and preprochymosin, as a result of the insert-DNA in the plasmid coding for the chymosin or its precursors.

Preferably, the lactic acid bacteria according to the invention belong to the genus Streptococcus, and most preferably they belong to the species of *Streptococcus cremoris*, *Streptococcus diacetilactis* or *Streptococcus lactis*.

A further embodiment of the invention relates to a process for preparing a fermented food product, animal feedstuff or ingredient thereof, in which process a lactic acid bacterium according to the invention is used, as well as to the products so obtained.

Another embodiment relates to a process for preparing a protein, in which process a lactic acid bacterium according to the invention is used, as well as to the protein so obtained.

The invention will be illustrated by the following six Examples without being limited thereto.

In Example 1 the construction of recombinant vector plasmids pGK1, pGK2 and pGK12 is described. They contain one (pGK1 and pGK11) or two (pGK12) markers beside the replication origin of *Streptococcus cremoris* Wg2 plasmid pWV01. Also the expression of the heterologous genes $Cm^R$ and $Em^R$ located on pGK12 in *B. subtilis*, *E. coli* and *Streptococcus lactis* is described.

In Example 2, the construction of recombinant vector plasmids with one (pGK3) and two (pGKV1 and pGKV2) markers beside the replication origin of pWV01 is described. Further, the expression of two heterologous genes (for $Em^R$ and CAT) is described. The latter gene derived from *Bacillus pumilus* was expressed under control of the *Bacillus subtilis* SPO2 promoter.

In Example 3, the cloning and expression of genes coding for *Streptococcus cremoris* protease(s) in *Bacillus subtilis* and *streptococcus lactis* are described using derivatives of pWV01, in particular pGKV500 containing the protease gene(s). The construction of pGD4, pGD6 and pGKV500 is also described.

In Example 4, the cloning and expression of a gene coding for prochymosin in *Streptococcus lactis* under control of a *Bacillus subtilis* promoter is described, as well as the construction of plasmids pGKV20, pGKV210, pGKV21, pGKV41 and pGKU1 which are used thereby.

In Example 5, growth and acid production of *Streptococcus lactis* MG1363 (which is Prt⁻) transformed to Prt⁺ by incorporation of pGKV500 are described.

In Example 6, a procedure is described to detect and isolate other protease genes by hybridization with the 5.0 Md BamHI fragment from pGD4 with the 1.4 Md BamHI/HindIII fragment from pGD6.

Thus, Examples 1–5 describe both recombinant vector plasmids (pGK1, pGK3, pGK11, pGK12, pGD4, pGD6, pGKV1, pGKV2, pGKV20, pGKV210, pGKV21, pGKV41) and recombinant plasmids containing an insert-DNA which can give improved or new properties to lactic acid bacteria (pGKV500 for protease activity and pGKU1 for milk-clotting activity).

The details of the isolation of the protease(s) of pWV05 and their expression in general, given in Examples 3 and 5, are not claimed in this application, but will form the subject of another patent application claiming the convention priority from this or a similar patent application as filed under the European Patent Convention on 4 Mar. 1985.

The details of the combination of Bacillus subtilis promoter SPO2 and the structural gene for prochymosin as given in Example 4 are not claimed in this application, but will form the subject of another patent application claiming the priority from this or a similar patent application filed under the European Patent Convention on 4 Mar. 1985.

However, Examples 3 and 5, relating to the expression of the protease gene(s) in Streptococcus lactis, and Example 4, relating to the expression of a chymosin precursor gene in Streptococcus lactis, illustrate the embodiment of the present invention related to the use of lactic acid bacteria transformed with recombinant plasmids, which give improved or new properties to the original lactic acid bacteria, and thus in the first place are Examples of the present invention.

Example 6 describes the use of the 5.0 Md BamHI fragment from pGD4 and the 1.4 Md BamHI/HindIII fragment from pGD6 as probes to detect and isolate other protease genes, which can be inserted into plasmids to give Prt$^+$ activity to Prt$^-$ lactic acid bacteria.

was used for plating. Chloramphenicol was used at concentrations of 5 and 2 µ/ml and erythromycin was used at concentrations of 5 and 50 µg/ml for B. subtilis and E. coli, respectively. M17-glucose broth and M17-glucose agar plates (see reference 14) were used to grow Streptococcus lactis. For Streptococcus lactis chloramphenicol and erythromycin were used at concentrations of 5 and 1 µ/ml, respectively.

Isolation of plasmid DNA

Plasmids pE194 cop-6 and pGL112 were isolated as described by de Vos et al. (see reference 15). Large-scale or mini preparations of recombinant plasmids from E. coli and of pWV01 and recombinant plasmids from B. subtilis were obtained by using the method of Ish-Horowicz and Burke (see reference 16). For B. subtilis some minor modifications were introduced. The cells were lysed in TES buffer (50 mM Tris-hydrochloride, 5 mM EDTA, 50 mM NaCl, pH 8.0) containing 20% sucrose and 2 mg of lysozyme per ml by 15 min of incubation at 0° C., followed by 15 min at 37° C. For large- or small-scale isolation of plasmid DNA from Streptococcus lactis the method of Gasson (see reference 8) was used.

Restriction enzyme reactions and purification of DNA fragments

TABLE A

Bacterial strains and plasmids

| designation of strain | chromosomal markers | plasmid | plasmid marker | mol. wt. (×10$^6$) | source, comments |
|---|---|---|---|---|---|
| B. subtilis | | | | | |
| 8G5 | trp tyr his ade met rib ura nic | — | | | Laboratory collection State University; Groningen (see reference 10) |
| 8G5 (pWV01) | | pWV01 | — | 1.5 | (see reference 5) |
| 8G5(pGL112) | | pGL112 | Cm$^R$ Km$^R$ | 2.4 | plasmid of Bron & Luxen$^a)$ Laboratory collection State University; Groningen |
| 8G5(pE194 cop-6) | | PE194 cop-6 | Em$^R$ | 2.3 | plasmid (see reference 11) |
| 8G5(pGK1) | | pGK1 | Cm$^R$ | 2.4 | described herein |
| 8G5(pGK11) | | pGK11 | Cm$^R$ | 2.1 | described herein |
| 8G5(pGK12) | | pGK12 | Cm$^R$ Em$^R$ | 2.9 | described herein |
| E. coli | | | | | |
| BHB2600 | 803 supE$^+$ supF$^+$ r$_k^-$ m$_k^+$ met$^-$ | | | | (see reference 12) |
| BHB2600(pGK12) | | pGK12 | Cm$^R$ Em$^R$ | 2.9 | described herein |
| Streptococcus lactis | | | | | |
| MG1363 | | | | | |
| MG1363(pGK12) | | pGK12 | Cm$^R$ Em$^R$ | 2.9 | described herein (see reference 8) |

$^a)$pGL112 is a chimera of pC194 and pUB110, constructed by S. Bron and E. Luxen, which contains the replication functions and the Km$^R$ gene of pUB110 and the Cm$^R$ gene of pC194.

EXAMPLE 1

Construction of derivatives of pWV01, notably plasmids pGK1, pGK11 and pGK12, which contain at least one marker beside the replication origin of pWV01, as well as expression of heterologous genes located on pGK12 in B. subtilis, E. coli and S. lactis.

MATERIALS AND METHODS

Bacterial strains and media

The strains used are described in Table A. For preparing plasmid DNA B. subtilis and E. coli cells were grown in TY broth (see reference 13). TY broth solidified with 1.5% agar Restriction enzymes were used as specified by the manufacturer. Digested DNA was analyzed in 1% horizontal agarose (Bio-Rad Laboratories, Richmond, Calif.) gels in TBE buffer (89 mM Tris, 89 mM boric acid, 2 mM EDTA, 0.5 µg of ethidium bromide per ml; pH 8.0). Bacteriophage SPP1 DNA digested with EcoRI served as a DNA size marker. DNA restriction enzyme fragments used for cloning were separated in agarose gels and were isolated and purified from the gels with a DEAE membrane (Schleicher & Schuell, Dassel, West Germany) according to the instructions of the supplier.

Molecular cloning and transformation

Vector molecules were mixed with the restriction fragments to be inserted at a ratio of approximately 1:2 at a concentration of 100 µ/ml in TE buffer (10 mM Tris-hydrochloride, 1 mM EDTA; pH 7.4). After heating for 5 min at 68° C., the samples were adjusted to ligase buffer (10 mM Tris-hydrochloride, 10 mM $MgCl_2$, 10 mM dithiothreitol, 1 mM ATP, 50 mM NaCl; pH 7.4). T4 DNA ligase was added, and the mixtures were incubated for 2 h at 7° C. After fivefold dilution with ligase buffer, incubation was continued for about 18 h at 7° C. Ligated DNA preparations were used to transform protoplasts of B. subtilis 8G5 by the method of Chang and Cohen (see reference 17). Transformants were selected on DM3 plate containing 5 µg of chloramphenicol or erythromycin per ml. B. subtilis 8G5 was grown to competence essentially as described by Bron and Venema (see reference 10). After exposure to the DNA, the cultures were diluted twofold with TY broth and were incubated for 90 min to allow for expression. Transformants were selected on TY plates containing 5 µg of chloramphenicol per ml or 5 µg of erythromycin per ml or both. Transformation of E. coli was performed by the method of Mandel and Higa (see reference 18). Protoplast transformation of Streptococcus lactis MG1363 was done as described by Kondo and McKay (see reference 19), except that 25% sucrose was used for stabilization of the protoplasts.

Plasmid copy number determination

B. subtilis was grown overnight in minimal medium consisting of Spizizen minimal salts (see reference 20) plus glucose (0.5%), casein hydrolysate (0.02%), and growth factors (14 µg each per ml, except for vitamins; vitamins, 0.4 µ/ml). M9-glucose minimal medium (see reference 21) supplemented with 0.02% casein hydrolysate and growth factors at concentrations of 20 µg/ml was used to grow E. coli. Streptococcus lactis was grown to late exponential phase in M17-glucose broth. All three media were supplemented with 5 µCi of [methyl-$^3$H]thymidine (New England Nuclear Corp., Boston, Mass.) per ml and the appropriate antibiotics. Total cell and plasmid DNA was isolated from 2-ml portions of the cultures by scaling down the plasmid DNA isolation procedure described by de Vos et al. (see reference 15) 100-fold. For Streptococcus lactis 10 ml of the culture was used with lysozyme at a concentration of 5 mg/ml. After the incubation step with pronase, the lysates were placed at −80° C. until frozen, heated for 5 min at 65° C., and agitated for two 30-s intervals with a Vortex mixer (top speed). Chromosomal and plasmid DNAs in the lysates were separated in a 0.8% agarose gel. The ethidium bromide-stained bands were excised and dissolved in a boiling water bath. After addition of 15 ml of Hydroluma (Lumac Systems Inc., Titusville, Pa.), the samples were counted in a Mark II liquid scintillation counter (Nuclear-Chicago Corp., Des Plaines, Ill.).

RESULTS

Genetic marking of pWV01

Figure 1:
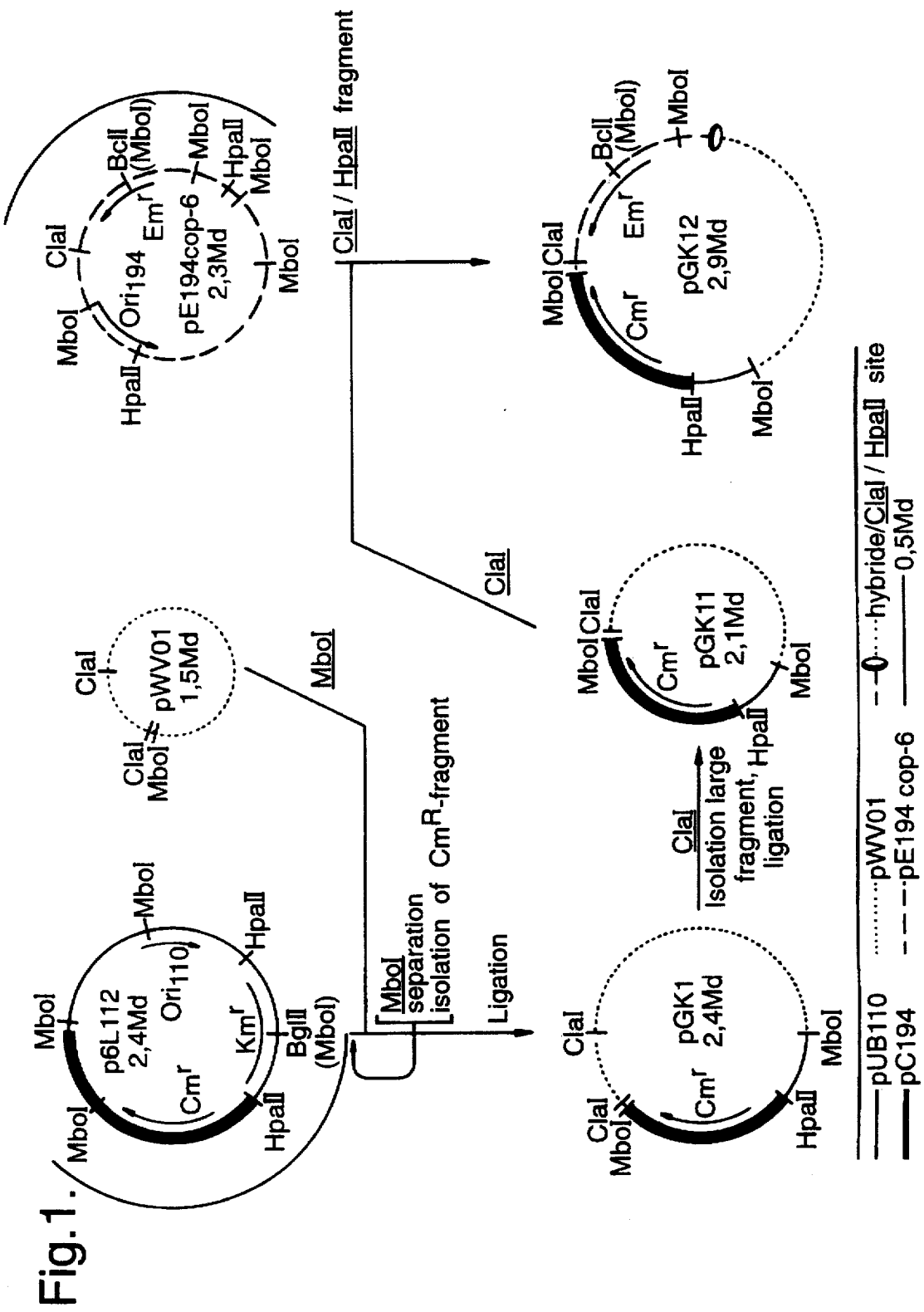
In FIG. 1 the restriction enzyme maps of plasmids pGK1, pGK11 and pGK12 are given as well as their preparation from plasmids pWV01, pGL112 (which is a chimera of plasmids pC194 and pUB110) and pE194 cop-6. pWV01 has a unique MboI site and two ClaI sites which can be used in further constructions. pGK1 has a unique HpaII site. pGK11 has unique ClaI and HpaII sites. pGK12 has unique BclII, ClaI and HpaII sites.

The physical maps of pGL112, pE194 cop-6, and pWV01 are presented in FIG. 1, together with the cloning strategy. pGL112 was digested with MboI, and the fragments were separated on a 1% agarose gel. The largest fragment comprises the pC194 sequence between residues 973 and 2,004 on the sequence of Horinouchi and Weisblum (see reference 3). It contains the entire chloramphenicol resistance ($Cm^R$) gene but lacks the origin of replication of pC194; it does not contain the origin of replication of pUB110 (see reference 22). This fragment was purified and ligated into the unique MboI site of pWV01, and the ligation mixture was used to transform protoplasts of B. subtilis. $Cm^R$ regenerants were obtained, and the plasmid of one of these, designated pGK1 (2.4 megadaltons [Md]), was characterized by restriction enzyme analyses. Digestion with MboI yielded two fragments, the largest of which migrated to the same position as the linear plasmid pWV01 (1.5 Md). The second fragment (0.9 Md) corresponded to the largest MboI fragment of pGL112. Digestion of pGK1 with ClaI generated the following two fragments: the unchanged small ClaI fragment of pWV01 (FIG. 1) and a 2.1-Md fragment which resulted from the insertion of the $Cm^R$ gene-containing fragment of pGL112 into the large 1.2-Md ClaI fragment of pWV01. The small ClaI fragment was deleted from pGK1 in vitro by cutting with ClaI. After isolation and religation of the largest fragment, protoplast transformation of B. subtilis with the ligation mixture yielded $Cm^R$ regenerants. These cells contained the deletion derivative of pGK1, which was designated pGK11 (2.1 Md) and had a unique ClaI site. As pGK1, this plasmid also contained a unique HpaII site, residue 973 on the sequence of Horinouchi and Weisblum (see reference 3), providing additional evidence that both recombinant plasmids carried the specific pGL112 MboI fragment. The orientation of this fragment in pGK1 was deduced from double digestion with ClaI and HpaII. The fact that the small ClaI fragment of pGK1 was deletable without impairing plasmid replication suggested that the remaining ClaI site in pGK11 could be used for cloning.

Construction of an insertion-inactivation vector

In order to examine the usefulness of the ClaI site for insertion and to further improve these pWV01-derived recombinant plasmids for cloning purposes, an insertion-inactivation vector was constructed from pGK11 (FIG. 1). To do this, pE194 cop-6 was digested with ClaI and HpaII, and the largest ClaI/HpaII fragment was isolated. This fragment, ranging from residues 1,939 to 3,137 on the sequence of Horinouchi and Weisblum (see reference 4), contains the erythromycin resistance ($Em^R$) gene and is devoid of the replication origin of pE194 cop-6. It was ligated into the unique ClaI site of pGK11. Transformation of protoplasts of B. subtilis with the ligation mixture resulted in $Cm^R$ $Em^R$ transformants. One of these was selected and contained a 2.9-Md plasmid. The results of a restriction enzyme analysis both of this plasmid, designated pGK12, and of the parental plasmid pGK11 were in agreement with FIG. 1. As a consequence of the ligation of the ClaI-HpaII insertion into ClaI-linearized pGK11, plasmid pGK12 still contained a unique ClaI site, as well as a unique HpaII site. pGK12 was linearized by BclI, confirming the identity of the insertion. The BclI site is situated in the coding sequence of the $Em^R$ gene, and insertion of DNA fragments into this site inactivates $Em^R$ (see reference 7). In addition, the presence of pWV01 sequences was confirmed by Southern hybridization (see reference 23) of the recombinants, using pWV01 isolated from Streptococcus cremoris Wg2 as a probe.

Replication of pGK12 and expression of heterologous genes in E. coli and B. subtilis The fact that the $Cm^R$ and $Em^R$ genes which are used to genetically mark plasmid pWV01, are both expressed in E. coli (see references 24 and 25) made it feasible to investigate whether the recombinant plasmids also replicate in this organism. To do this, competent cells of E. coli BHB2600 were exposed to plasmid pGK12. After allowing time for expression, dilutions were plated onto TY agar plates containing 2 µg of chloramphenicol per ml and 50 µg of erythromycin per ml. After overnight incubation small colonies appeared. These colonies contained plasmid DNA indistinguishable from pGK12 isolated from B. subtilis with respect to size and restriction enzyme patterns. The combination of 2 µg of chloramphenicol per ml and 50 µg of erythromycin per ml was appropriate to select for transformed E. coli BHB2600 cells. With erythromycin or chloramphenicol alone, 100 µg or more of erythromycin per ml or up to 10 µg of chloramphenicol per ml is needed for selection, depending on the E. coli strain used. pGK12 isolated from E. coli transformed competent B. subtilis cells to $Cm^R$ and $Em^R$ with normal frequencies. Transformation of B. subtilis to $Cm^R$ $Em^R$ required induction of the cells with 50 ng of erythromycin per ml during the expression time. Without induction, transformants could only be scored on plates containing chloramphenicol alone.

The transformation efficiency of pGK12 from both sources in transformations of *B. subtilis* and *E. coli* competent cells is shown in Table B, which shows that the transforming activity on either host is independent of the source of the plasmid DNA.

TABLE B

Transformation of *B. subtilis* 8G5 and *E. coli* BHB2600 competent cells with plasmid pGK12 DNA, isolated from either *B. subtilis*, or *E. coli*

| recipient | Donor source of pGK12 | |
|---|---|---|
| | *B. subtilis* | *E. coli* BHB2600 |
| *B. subtilis* 8G5 | $4.1 \times 10^{-3}$ | $8.7 \times 10^{-3}$ |
| *E. coli* BHB2600 | 0.16 | 0.22 |

Replication of pGK12 and expression of heterologous genes in *Streptococcus lactis*

To examine whether the markers carried by the pWV01-derived vectors can be expressed in lactic acid streptococci, pGK12 isolated from *B. subtilis* was used to transform protoplasts of *Streptococcus lactis* MG1363, a plasmid-free strain (see reference 8). Protoplasts of *Streptococcus lactis* MG1363 were prepared as described by Kondo and McKay (see reference 19) and treated with 1 µg of pGK12. After 2 h of incubation at 30° C. to allow time for expression, dilutions were plated onto sucrose-M17 plates containing either 5 µg of chloramphenicol per ml or 1 µg of erythromycin per ml. After incubation at 30° C. for about 7 to 10 days, colonies appeared on both types of plates. $Cm^R$ colonies were also $Em^R$ and vice versa. In a typical experiment, regeneration was 10%, and the number of transformants per microgram of pGK12 was about $0.5 \times 10^4$. Transformant colonies contained a plasmid which had the same molecular weight and restriction enzyme patterns as pGK12.

Copy numbers and plasmid stability

The copy number of pGK12 in the three hosts was determined (see Table C).

TABLE C

Estimation of pGK12 copy number in *B. subtilis*, *E. coli* and *Streptococcus lactis**

| Strain | A total circular DNA (cpm) | B chromosomal DNA (cpm) | ratio B/A | pGK12 copy number |
|---|---|---|---|---|
| *B. subtilis* 8G5 (pGK12) | 124 | 15,823 | 128 | 5 |
| *E. coli* BHB2600 (pGK12) | 3,723 | 54,319 | 15 | 62 |
| *Streptococcus lactis* MG1363 (pGK12) | 8,975 | 1,804,020 | 201 | 3 |

*Lysates of plasmid-carrying strains were prepared and analyzed as described in the text. To calculate the copy numbers (plasmid molecules per chromosome equivalent), the molecular weights of the *B. subtilis*, *E. coli* and *Streptococcus lactis* chromosomes were taken as $2.0 \times 10^9$, $2.7 \times 10^9$, and $1.7 \times 10^9$, respectively (see references 26 and 27).

In both *Streptococcus lactis* and *B. subtilis* pGK12 was maintained at a low copy number; in *B. subtilis* it was about 5, which is in good agreement with the value found for pWV01 in *B. subtilis* (see reference 5). The copy number of pGK12 in *E. coli* was approximately 10 times higher than that in *B. subtilis*.

TABLE D

| Plasmid stability* | | |
|---|---|---|
| Strain | Number of colonies scored | % $Cm^S$ $Em^S$ |
| *B. subtilis* 8G5 (pGK12) | 133 | 3 |
| *E. coli* BHB2600 (pGK12) | 209 | 48 |
| *Streptococcus lactis* MG1363 (pGK12) | 226 | 0 |

*An overnight TY-broth culture supplemented with the appropriate antibiotics was diluted $10^5$, grown for 18 h at 37° C. (30° C. for *Streptococcus lactis*) in TY-broth without antibiotics, and then plated onto non-selective medium. Colonies were replica-plated onto TY-plates containing chloramphenicol and erythromycin.

Table D shows that pGK12 was stably maintained in *Streptococcus lactis* and *B. subtilis* in the absence of selective pressure. This is in contrast to *E. coli*, which lost pGK12 at a frequency of 48%. pGK12 conferred resistance to at least 2 mg erythromycin per ml in all three organisms. The resistance levels for chloramphenical were approximately 5, 10, and 50 µ/ml in *Streptococcus lactis*, *E. coli*, and *B. subtilis*, respectively.

EXAMPLE 2

Expression of genes in *S. lactis* under control of a *B. subtilis* promotor [Description of the construction of plasmids pGK3, pGKV1 and pGKV2]

Construction of pGK3 (See also FIG. 2)

Various methods used in this example are given in all detail either in example 1 or example 3. *S. cremoris* Wg2 plasmid pWV01 was treated with restriction enzyme ClaI and the largest ClaI fragment, containing the origin of replication of pWV01, was isolated. Plasmid pE194-cop-6 was treated with restriction enzymes ClaI and HpaII and the largest ClaI/HpaII fragment, containing the $Em^R$ gene, was isolated. These two fragments were subsequently ligated to each other. As the sticky ends of ClaI and HpaII fit to each other, two plasmids were obtained in this way. The plasmid in which the restored ClaI site was located close to the MboI site of the largest ClaI fragment of pWV01 was called pGK3.

Construction of pGKV1 and pGKV2 (See also FIG. 2)

Plasmid pGK3 was treated with restriction enzyme ClaI and the sticky ends were filled up using the Klenow fragment of *E. coli* DNA polymerase I.

The *B. subtilis* plasmid pPL608 (see reference 9) carrying the chloramphenicol acetyl transferase (CAT) gene of *B. pumilus* was completely digested with restriction enzyme PvuII and subsequently partially digested with EcoRI restriction endonuclease.

The largest PvuII/EcoRI fragment containing the SPO2 promotor and the CAT gene was isolated by electro-elution from the agarose gel.

The EcoRI cohesive end of the PvuII/EcoRI fragment was filled up using the Klenow fragment of *E. coli* DNA polymerase I.

This PvuII/EcoRI fragment and the ClaI- and Klenow-treated pGK3 were blund-end ligated to each other. The blund-end ligation of the filled ClaI and EcoRI sites resulted in a new EcoRI site.

Subsequently, protoplasts of *B. subtilis* PSL1 were exposed to the ligation mixture according to Chang et al. (see reference 17) and $Em^R$ and $Cm^R$ transformants were selected.

Two types of transformants were obtained, one carrying plasmid pGKV1 and the other carrying plasmid pGKV2 (a restriction map of both plasmids is shown in FIG. 2). The difference between pGKV1 and pGKV2 concerns the orientation of the CAT gene towards the SPO2 promoter.

These vectors were used to transform protoplasts of *S. lactis*.

The fact that the transformed *S. lactis* was $Cm^R$ beside $Em^R$ proved that the SPO2 promotor of *B. subtilis* functioned in *S. lactis* and therefore can be used to bring other heterologous genes to expression.

EXAMPLE 3

Cloning and expression of genes coding for *S. cremoris* protease(s) in *B. subtilis* and *S. lactis* using derivatives of pWV01 [Description of the construction of pGKV500]
Bacterial strains, plasmids and media The strains and plasmids used are described in Table E.

TABLE E

Bacterial strains and plasmids[a]

| Bacterial strain or plasmid | Relevant phenotype/ genotype | Remarks; plasmid Mol. wt (×10⁶) | Source |
|---|---|---|---|
| *B. subtilis* PSL1 | arg leu thr r⁻ m⁻ stp recE4 | | see ref. 28 |
| *E. coli* C600 | thr leu thi lacY tonA phx supE vtr | | PC[b] |
| *S. cremoris* | | plasmids: | |
| Wg2 | Prt⁺ | 16.0; 11.5; 6.1; 2.9; 1.5 | see ref. 1 |
| Wg2 | Prt⁻ | 11.5; 2.9; 1.5 | see ref. 1 |
| HP | Prt⁻ | 25; 17.7; 9; 3.4; 1.9 | see ref. 29 |
| HP | Prt⁻ | 25; 17.7; 3.4; 1.9 | see ref. 29 |
| *S. lactis* | | plasmids: | |
| NCDO712 | Lac+ Prt+ | 33; 9; 5.2; 2.5; 1.8 | see ref. 8 |
| MG1363 | Lac⁻ Prt⁻ | Plasmid-free derivative of *S. lactis* NCDO712 | see ref. 8 |
| Plasmid pBR329 | $Cm^R$ $Ic^R$ $Ap^R$ | | see ref. 30 |
| pACYC184 | $Cm^R$ $Tc^R$ | | see ref. 31 |
| pGD4 | $Cm^R$ | 5.0 Md BamHI fragment of pWV05 cloned in pACYC184 | described herein |
| pGD6 | $Cm^R$ $Ap^R$ | pBR329 containing among others, the 1.4 Md BamHI/ HindIII fragment of pWV05 | described herein |
| pGKV2 | $Cm^R$ $Em^R$ | Double resistence vector, constructed from the cryptic *S. cremoris* plasmid pWV01 | described herein |
| pGKV500 | $Em^R$ | 4.3 Md HindIII fragment of pWV05 cloned in pGKV2 | described herein |

[a]abbreviations: Cm: chloramphenicol; Em: erythromycin; Tc: tetracyclin; Ap: ampicilin
[b]PC: Phabagen Collection.

*B. subtilis* and *E. coli* cells were grown in TY-broth. TY-broth solidified with 1.5% agar was used for plating. Chloramphenicol and erythromycin were used at 5µg/ml for *B. subtilis*, chloramphenicol, ampicillin and tetracyclin at 40, 30 and 12.5/µg/ml for *E. coli*, respectively. Glucose-M17-broth and agar (see reference 14) were used to grow *S. lactis*. With *S. lactis*, chloramphenicol and erythromycin were used at 4 µ/ml and 1 µ/ml, respectively. *S. cremoris* Wg2 and *S. cremoris* HP were routinely maintained in sterile 10% (wt/vol) reconstituted skim milk. Glycerophosphate-milk-agar (see reference 32), slightly modified by the addition of 0.001% bromocresol purple and citrate-milk-agar (see reference 32a) were used to test the ability of *S. lactis* strains to utilize milk protein.

Isolation of plasmid DNA

Plasmids from *E. coli* were isolated as described by Ish-Horowitz et al. (see reference 16). Plasmid DNA from *B. subtilis* was isolated as described in Example 1. This method also proved useful for mini-preparations of plasmids from *S. lactis*. The method of LeBlanc et al. (see reference 33) was used to isolate plasmids from *S. cremoris* Wg2 and *S. cremoris* HP.

Isolation of pWV05

Total plasmid from *S. cremoris* Wg2 was separated in 0.5% agarose gels using Tris-acetate buffer (40 mM Tris-acetate, 20 mM sodium acetate, 2 mM EDTA; pH 7.8). pWV05 was excised from the gels and processed for KI-gradient centrifugation as described by Blin et al. (see reference 34) with the following modifications: gel slices were frozen (−20° C.), thawed and to 6.5 g of slices approximately 12 g solid KI was added. After mixing on a bloodcell suspension mixer to dissolve all agarose, 0.1 ml ethidium bromide (5 mg/ml) was added, and the solution was adjusted to a refractive index of 1.444. The gradients were centrifuged for 20 h at 53,000 rpm in a Beckman type 75 Ti fixed angle rotor at 20° C. A second run was needed to remove all agarose from the DNA band.

Restriction enzyme analysis and molecular cloning

Restriction enzymes and T4 DNA ligase were purchased from Boehringer (Mannheim, F.R.G.) and used according to the supplier's instructions. Digested DNA preparations were electrophoresed in horizontal agarose gels (0.5 to 1%) in TBE buffer (89 mM Tris, 89 mM boric acid, 2 mM EDTA, 0.5 µ/ml ethidium bromide; pH 8.0). Restriction enzyme fragments of pWV05 were shot-gun cloned in pBR329 or in pACYC184 using KI-purified pWV05. Alternatively, specific fragments were purified from a digest of total *S. cremoris* Wg2 plasmid DNA by agarose gel electrophoresis and subsequent electro-elution. Competent cells of *E. coli* were transformed according to Mandel et al. (see reference 18). Protoplasts of *B. subtilis* were transformed as described by Chang et al. (see reference 17). *S. lactis* protoplasts were prepared using a modification of the method of Okamoto et al. (see reference 35). An overnight glucose-M17 culture was diluted 100-fold in glucose-M17 and incubated for 2 h at 30° C. The cells were washed in TMS (30 mM Tris-HCl, 3 mM $MgCl_2$, 25% sucrose; pH 8.0) and resuspended to half of the original volume in TMS+30 µ/ml lysozyme. After incubation for 1 h at 37° C., the protoplasts were washed in SMM (25% sucrose, 20 mM $MgCl_2$, 20 mM maleate; pH 6.5) and resuspended in SMM to ⅟₃₀ of the original volume. Protoplast transformation was done as described in Example 1, except that protoplasts and DNA were incubated for 20 min at room temperature in 22.5% polyethylene glycol.

Subcloning of plasmid pWV05

Figure 3:
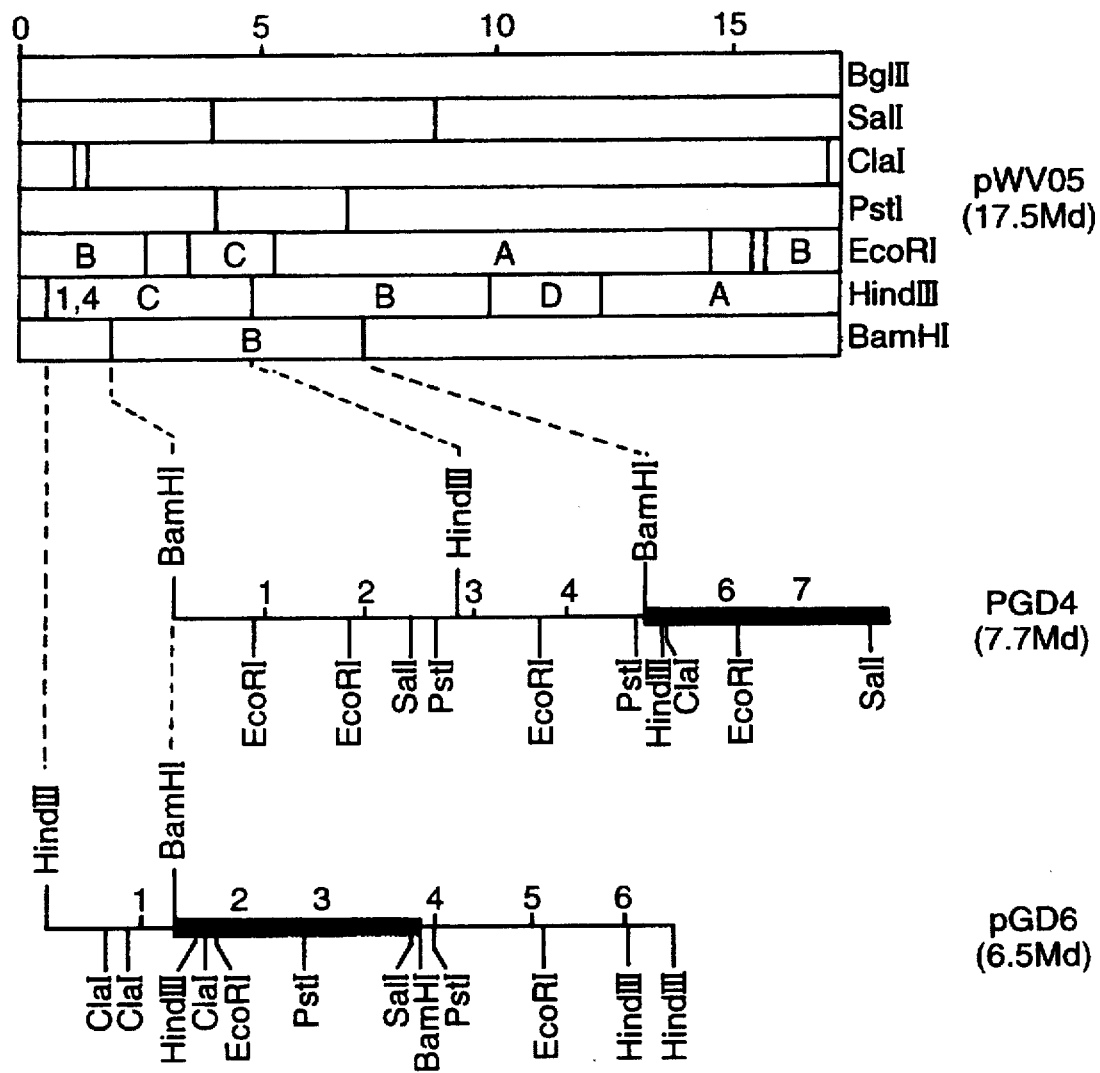
In FIG. 3 a linear restriction enzyme map of plasmid pWV05 is given for BamHI, BglII, ClaI, EcoRI, HindIII, PstI and SalI. Further linear restriction enzyme maps of plasmids pGD4 and pGD6 are given with the relation to the fragments of pWV05 which are present in pGD4 and pGD6. The vector DNA in pGD4 and pGD6 (from pACYC184 and pBR329, respectively) is shown in bold lines.

Gel electrophoresis of the total plasmid DNA of *S. cremoris* Wg2 and subsequent KI-gradient centrifugation of the excised pWV05 bands yielded approximately 1.5 µg of pWV05 per liter of culture. A restriction enzyme map derived from simultaneous or sequential digestions of purified pWV05 with several restriction endonucleases is presented in FIG. 3. *E. coli* plasmids pBR329 (2.69 Md) and pACYC184 (2.65 Md) were used to clone parts of pWV05. BamHI fragment B (5.0 Md) was cloned in pACYC184 (giving plasmid pGD4; see FIG. 3) as were EcoRI fragments A (9.0 Md) and C (2.0 Md) (not shown). HindIII fragments A (5.2 Md), B (5.1 Md) and D (2.6 Md) were cloned into pBR329 (not shown). The HindIII fragment C (4.3 Md) and the EcoRI fragment B (4.6 Md) were never found among the recombinant vectors obtained, neither after shotgun cloning nor after ligation of the specific fragments to the vector DNA. To clone the remaining part of pWV05, a BamHI/HindIII double digest of total S. cremoris Wg2 plasmid DNA was ligated to BamHI/HindIII cut pBR329. One recombinant was picked up which contained the 1.4 Md BamHI/HindIII fragment constituting the left part of HindIII fragment C. The right-hand BamHI/HindIII fragment B and a 0.5 HindIII fragment of unknown origin were also present in this scrambled plasmid (pGD6 in FIG. 3). These results, showing that breaking of the continuity of the HindIII fragment C and the EcoRI fragment B enabled the cloning of their subfragments in E. coli, suggest that either a particular property of the DNA sequence interfered with plasmid stability or that expression of this DNA interfered with the viability of E. coli.

Crossed immunoelectrophoresis

B. subtilis and S. lactis were grown overnight in 500 ml TY-broth containing 5 μ/ml erythromycin and in glucose-M17-broth with 1 μ/ml erythromycin, respectively. Cells were harvested by centrifugation, washed with cold (4° C.) 50 mM potassium phosphate (pH 6.8) and resuspended in 2 ml of the same buffer, containing 1 mM EDTA. The cells were disrupted by sonication. Triton X-100 was added to a final concentration of 4% and, after incubation for 30 min at room temperature, cell debris was removed by centrifugation for 15 min at 15,000 rpm in a Beckman SW41 rotor at 4° C. The cell-free extracts were concentrated by acetone precipitation. Protein concentration was determined by the method of Bradford (see reference 36). Crossed immunoelectrophoresis of the cell-free extracts in the presence of antibodies raised against the purified proteins of the S. cremoris Wg2 proteolytic system was carried out as described previously (see reference 37). The gels were run in the first dimension at 2.5 V/cm for 3 h and at 1.5 V/cm for 16–18 h in the second dimension.

Figure 4:
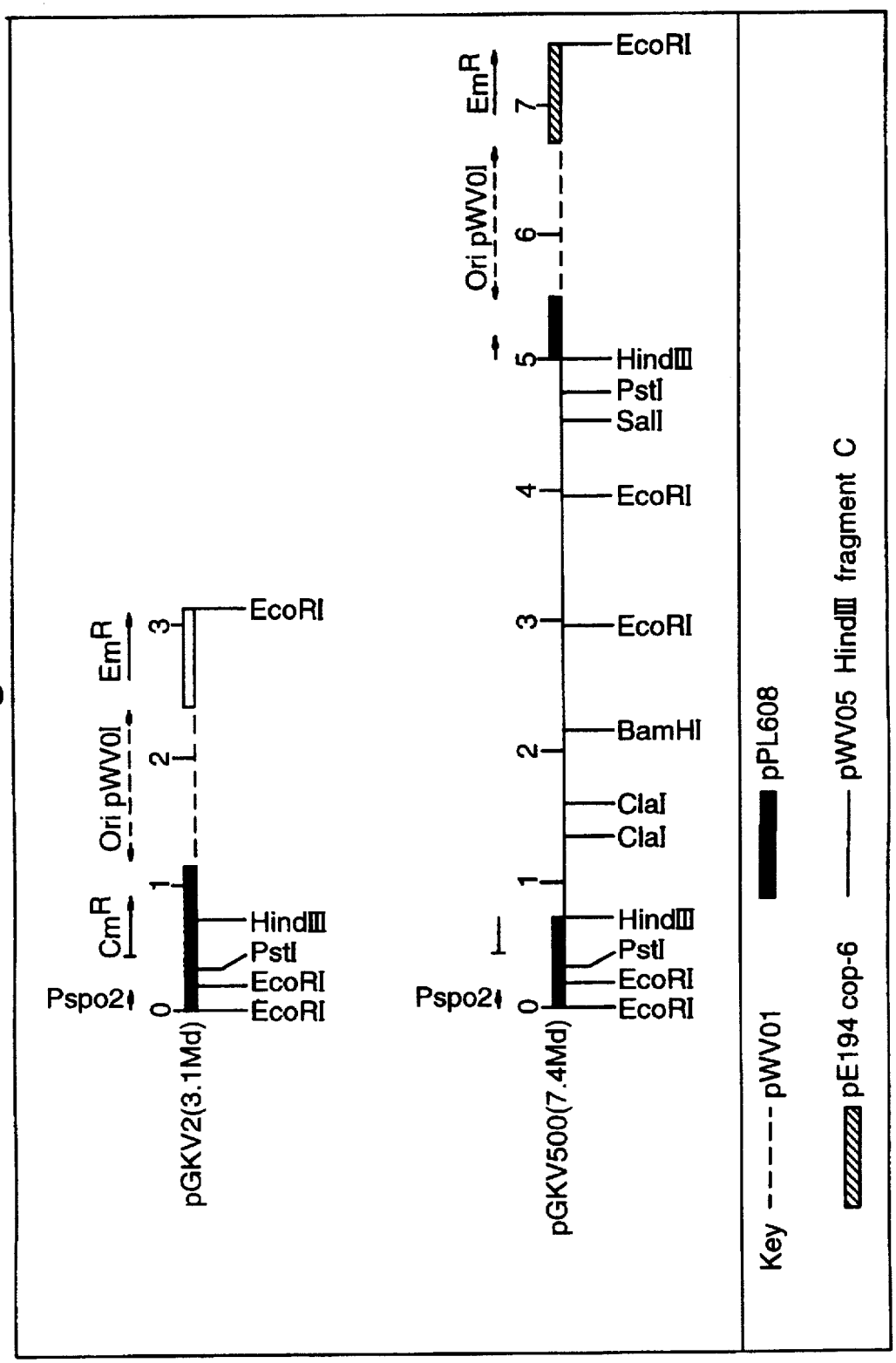
In FIG. 4 linear restriction enzyme maps of plasmids pGKV2 and pGKV500 are given and the origin of the fragments of the plasmids.

Construction of pGKV500 pGKV2 (FIG. 2) contains a unique HindIII site in the coding sequence of chloramphenicol acetyl transferase (CAT). This site was used to insert the 4.3 Md HindIII fragment C, electrophoretically purified from a HindIII digest of S. cremoris plasmid pWV05. This construction resulted in pGKV500 (7.4 Md). Restriction enzyme maps of this plasmid and pGKV2 are shown in FIG. 4. The maps are linearized at the same EcoRI site to map at zero position.

Transfer of plasmid pGKV500 to S. lactis pWV01-derived vectors transform B. subtilis as well as E. coli and S. lactis. Therefore, pGKV500 isolated from B. subtilis was used to transform protoplasts of S. lactis MG1363, a plasmid-free strain, unable to ferment lactose and to produce proteinase because of the loss of a 33 Md lactose/proteinase plasmid. Rapid plasmid DNA extraction performed on 5 randomly picked transformants revealed that they all contained a plasmid with the same molecular weight as pGKV500 from B. subtilis.

Characterization of protein specified by the HindIII fragment C

From one of these S. lactis strains carrying pGKV500 and from B. subtilis (pGKV500) cell-free extracts were prepared and analysed in crossed immunoelectrophoresis (CIE) experiments. Extracts separated in the first dimension reacted with antibodies raised against the proteins of the purified proteolytic system of S. cremoris Wg2 (Prt⁺) in the second dimension. CIE patterns of:

FIG. 5 A. cell-free extract of B. subtilis PSL1 (pGKV500);

B. purified proteolytic system of S. cremoris Wg2;

C. tandem CIE of cell-free extracts of B. subtilis PSL1 (pGKV500) and of purified proteolytic system of E. cremoris Wg2 applied in one well;

D. same as C, but applied in right and left well, respectively;

FIG. 6 A. cell-free extract of S. lactis MG1363 (pGKV2);

B. cell-free extract of S. lactis MG1363 (pGKV500).

In A to D (FIG. 5) 1 μl of the B. subtilis extract (42 μg protein/ml) and 3 μl of the S. cremoris isolate (210 μg protein/ml) were used. The second dimension gel contained 30 μl of 28 mg/ml antibody against the proteolytic system of S. cremoris Wg2.

In A and B of FIG. 6, 15 μl of the S. lactis MG1363 (pGKV2) extract (45 mg protein/ml) and 15 μl of the S. lactis MG1363 (pGKV500) (53 mg protein/ml) were used. The second dimension gel contained 30 μl of 28 mg/ml antibody against S. cremoris Wg2 proteolytic system.

The CIE pattern of B (FIG. 5) shows the two major precipitation lines of the S. cremoris Wg2 proteolytic system, denoted A and B. Protein A has been found to possess caseinolytic properties. A weak line at the left of A and B is an impurity not related to the proteolytic system. The CIE patterns of A (FIG. 5) and B (FIG. 6) show that B. subtilis PSL1 (pGKV500) and S. lactis MG1363 (pGKV500) also produce two proteins which precipitate with the antibodies. Both proteins were absent in S. lactis MG1363 (pGKV2) (Cie pattern A [FIG. 6]) and B. subtilis PSL1 (pGKV2) (not shown). The precipitation lines running off the gel in the S. lactis MG1363 extracts (Cie patterns A and B [FIG. 6]) were present in both S. lactis MG1363 (pGKV2) and S. lactis MG1363 (pGKV500) and are, therefore, not insert-specified. The relationship between the insert-specified proteins and proteins A and B of S. cremoris Wg2 was examined in tandem CIE experiments.

With the B. subtilis PSL1 (pGKV500) extract and the S. cremoris Wg2 isolate loaded in the same sample hole (CIE pattern C) only two peaks were visible, suggesting that the proteins in the upper and lower peak of B. subtilis PSL1 (pGKV500) are the components A and B of the S. cremoris Wg2 proteolytic system, respectively. The observation that the surface under the two tandem peaks was roughly the sum of the individual peaks strengthens this views. CIE pattern D shows the result of a tandem CIE when the sample was applied on the same gel in adjacent holes.

The complete fusion of S. cremoris Wg2 peak B with the B. subtilis PSL1 (pGKV500) upper peak resulted in a higher and broader upper peak. Protein A from S. cremoris Wg2 shares common features with the protein in the lower precipitation line in both the B. subtilis PSL1 (pGKV500) and the S. lactis MG1363 (pGKV500) preparations: in both cases the peaks partially fused, the extract peak being lifted up.

EXAMPLE 4

The cloning and expression of a gene coding for prochymosin in S. lactis under control of a B. subtilis promoter [The construction of pGKV20, pGKV210, pGKV21, pGKV41 and pGKU1, see FIG. 7 and 8]

In order to construct a versatile cloning vector, the multiple cloning site (MCS) of M13mp11 (see reference 38) was inserted in between the SPO2 promoter and the CAT gene of plasmid pGKV2 (FIG. 7). Therefore, this plasmid was treated with the restriction enzyme EcoRI and ligated under diluted conditions, favouring the in-internal ligation of DNA molecules. After transformation of the ligation mixture to E.

coli BHB2600, transformants are obtained that contain the largest EcoRI fragment of pGKV2 as a plasmid designated as pGKV20. Plasmid pGKV20 and the replicative form (RF) of phage M13mp11, were digested with the restriction enzymes EcoRI and PstI. The largest EcoRI/PstI fragment of pGKV20 and the 38 bp EcoRI/PstI fragment of the MCS were isolated and ligated to form pGKV210.

Subsequently the SPO2 promoter was placed again in front of the CAT gene. The smallest EcoRI fragment of pPL608 was isolated from an EcoRI digest of this plasmid and ligated to EcoRI treated pGKV210 to form pGKV21. Since the SPO2 promoter-containing fragment can be situated in two orientations, colonies were selected for $Cm^R$ upon transformation. The resulting transformants must contain a plasmid in which the direction of the promoter allows transcription of the CAT gene. To facilitate further constructions, the BamHI site of the MCS in pGKV21 was converted into a ClaI site. pGKV21 was treated with the restriction enzyme BamHI, the sticky ends were filled in with the Klenow fragment of E. coli DNA polymerase I and the blunt ends obtained were ligated under diluted conditions to facilitate internal ligation. The resulting plasmid, which contains a ClaI site formed by the blunt end ligation of the filled in BamHI sites, is designated as pGK41. In this plasmid, part of the CAT gene was substituted with the gene coding for prochymosin. This gene is situated on plasmid pMS48 and is preceded on this plasmid by a B. subtilis Ribosome Binding Site (RBS) and the signal sequence of the alpha-amylase gene of B. amyloliquefaciens. It is brought to expression in B. subtilis under control of the SPO2 promoter. The whole gene containing the RBS, alpha-amylase signal sequence and prochymosin coding sequence was inserted in pGK41 as follows.

pMS48 was treated with the restriction enzyme BstEII and the sticky ends were filled in with the Klenow fragment of E. coli DNA polymerase I. Subsequently, the plasmid was treated with the restriction enzyme HindIII and the about 1 Md fragment containing, inter alia, the prochymosin gene was isolated. pGK41 was treated with the restriction enzyme ClaI and the sticky ends were also filled in with the Klenow fragment of E. coli DNA polymerase I. The linearised plasmid was treated with the restriction enzyme HindIII and the large fragment containing, inter alia, the origin of pWV01 and the gene coding for $Em^R$ was isolated. Ligation of both fragments resulted in one plasmid called pGKU1, in which the gene coding for prochymosin is brought under control of the SPO2 promoter. By the blunt-end ligation of the filled in ClaI and BstEII sites, the BstEII site is restored. This plasmid was transferred to S. lactis MG1363 and Western blots (see reference 39) indicated that the "pre"prochymosin was expressed in S. lactis under control of the B. subtilis SPO2 promoter.

A similar construction as has been outlined above can be carried out with the BstEII-HindIII fragment of pMS50 instead of the BstEII-HindIII fragment of pMS48.

EXAMPLE 5

Growth and acid production of S. lactis MG1363 transformed with pGKV500
Procedure Overnight cultures grown in glucose-M17-broth were washed in sterile distilled water and diluted 100-fold in skim milk (10% wt/vol) containing 0.5% glucose. Samples were taken at 1 h intervals during incubation at 30° C. Colony-forming units were determined by plating on glucose-M17-agar and acidity was determined by neutralization with 0.1N NaOH.

Phenotype of S. lactis (pGKV500) in milk

Lactic streptococci are nutritionally fastidious and require an exogenous supply of many amino acids. The concentration of free amino acids and small peptides in milk limits growth and concomitant acid production. For optimal growth, lactic streptococci are dependent on their proteinases which hydrolyze milk protein. Media developed to differentiate between proteinase-positive and proteinase-negative variants rely on their difference in growth and acid production in milk. To investigate whether the HindIII fragment of pGKV500 could restore good growth and acid production in a Prt⁻ host S. lactis MG1363, growth on milk-based agar plates and acid production in milk of S. lactis MG1363 (pGKV500) were examined. When suspended in transparent citrated milk agar, S. lactis MG1363 (pGKV500) forms typical large Prt⁺ colonies surrounded by a white precipitate of casein caused by rapid growth and acidification (see FIG. 9). S. lactis MG1363 (pGKV2) only forms very small colonies characteristic of the Prt⁻ phenotype, even after prolonged incubation at 30° C.

On GMAB medium, S. lactis MG1363 (pGKV500) gives large bright yellow colonies with a yellow halo, whereas S. lactis MG1363 (pGKV2) forms smaller colonies, white or faintly yellow, without a halo.

Growth and acid production in milk of S. lactis MG1363 (pGKV500), S. lactis MG1363 (pGKV2) and S. cremoris Wg2 were compared. S. lactis 712, the parental strain of the plasmid-free S. lactis MG1363 strain used throughout this study, carrying the 33 Md lactose/proteinase plasmid pLP712 (see reference 8), was also included in this comparison (FIG. 10).

This example proved that host cells transformed with plasmids containing genes for metabolic functions can grow better or are more active than the plasmid-free cells.

Lactose is the normal carbon source of lactic acid bacteria and therefore it is attractive to use one or several genes of the lactose metabolism as marker on plasmids.

It may be expected that integration of the large BclI fragment B of pLP712—containing the genes involved in the lactic metabolism (see reference 8)—into the BclI site of the $Em^R$ gene of pGKV41 or pGKV500 will result in a plasmid that gives a lac⁻ host cell the property to grow well without any other selection pressure in milk or similar substrates.

EXAMPLE 6

The use of the 5.0 Md. BamHI fragment from pGD4 and the 1.4 Md BamHI/Hind III fragment from pGD6 as probes to detect and isolate other protease genes.

On the basis of the pH- and temperature optima of their proteinases (proteases), S. cremoris strains are divided into five different groups. According to this classification S. cremoris strains HP and Wg2 belong to the same group (see ref. 40).

Furthermore, it has been reported that S. cremoris HP carries a 9 Md proteinase plasmid (see ref. 41). To investigate whether the 5.0 Md BamHI-fragment from pGD4 and the 1.4 Md BamHI/HindIII fragment from pGD6 could be used as probes to detect and isolate homologous or partly homologous proteinase genes of other sources the following experiment was carried out. The 5.0 Md BamHI fragment from pGD4 and the 1.4 Md BamHI/HindIII fragment from pGD6 were isolated from restriction enzyme digests from both plasmids. They were nick translated with [alpha-$^{32}$P] dCTP (see ref. 42) and used as probes in Southern hybridisations (see ref. 23). To test the procedure the probes were used on total plasmid of proteinase-proficient and proteinase-deficient *S. cremoris* Wg2. Both BamHI- and BamHI/HindIII fragments hybridized only with pWV05 of *S. cremoris* Wg2 (Prt⁺) and gave no signal with *S. cremoris* Wg2 (Prt⁻), indicating that no other homologous or partly homologous proteinase genes were located on other plasmids of *S. cremoris* Wg2 (Prt⁺) and that the BamHI- and BamHI/HindIII fragments really originate from pWV05.

Furthermore, both fragments did not hybridize with the plasmids of *S. cremoris* HP (Prt⁻). They did, however, hybridize to the 9 Md plasmid present in *S. cremoris* HP (Prt⁺), proving that indeed this plasmid contains a gene homologous to the proteinase gene(s) of pWV05.

The next step will be to make a restriction enzyme digest of the 9 Md plasmid to determine the fragment(s) on which the proteinase gene(s) of *S. cremoris* HP are located. So using the whole gene or fragments of the proteinase gene(s) of pWV05 one may be able to detect and isolate easily other homologous or partly homologous proteinase genes of other lactic acid bacteria.

Both a *Bacillus subtilis* strain 8G-5 (pGK12) containing plasmid pGK12 with accession number DSM 3239 and a *Bacillus subtilis* strain PSL-1 (pGK500) containing plasmid pGK500 with accession number DSM 3240 were deposited under the BUDAPEST TREATY with DEUTSCHE SAMMLUNG VON MICROORGANISMEN
Grisebachstrasse 8
D-3400 Goettingen
Germany.

REFERENCES CITED IN THE SPECIFICATION

1. Otto, R., W. M. de Vos, and J. Gavrieli. 1982. Plasmid DNA in *Streptococcus cremoris* Wg2: Influence of pH on Selection in chemostats of a variant lacking a protease plasmid. Appl. Environ. Microbiol. 43:1272–1277.
2. Wouters, J. T. M., and J. Stadhouders. 1982. Genetica van melkzuurbacteriën; een weg tot nieuwe toepassingen? Voedingsmiddelentechnologie 15:(no. 24)19–21 and (no. 26)26–28.
3. Horinouchi, S., and B. Weisblum. 1982. Nucleotide sequence and functional map of pC194, a plasmid that specifies inducible chloramphenicol resistance. J. Bacteriol. 150:815–825.
4. Horinouchi, S., and B. Weisblum. 1982. Nucleotide sequence and functional map of pE194, a plasmid that specifies inducible resistance to macrolide, lincosamide, and streptogramin type B antibiotics. J. Bacteriol. 150:804–814.
5. Vosman, B., and G. Venema. 1983. Introduction of a *Streptococcus cremoris* plasmid in *Bacillus subtilis*. J. Bacteriol. 156:920–921.
6. Lacey, R. W., and I. Chopra. 1974. Genetic studies of a multi-resistant strain of *Staphylococcus aureus*. J. Med. Microbiol. 7:285–297.
7. Horinouchi, S., and B. Weisblum. 1980. Post-transcriptional midification of mRNA conformation: mechanism that regulates erythromycin-induced resistance. Proc. Natl. Acad. Sci. USA 77:7079–7083.
8. Gasson, M. J. 1983. Plasmid complements of *Streptococcus lactis* NCDO 712 and other lactic streptococci after protoplast-induced curing. J. Bacteriol. 154:1–9.
9. Williams, D. M., E. J. Duvall and P. S. Lovett. 1981. Cloning restriction fragments that promote expression of a gene in *Bacillus subtilis*. J. Bacteriol. 146:1162–1165.
10. Bron, S., and G. Venema. 1972. Ultraviolet inactivation and excision-repair in *Bacillus subtilis*. I. Construction of a transformable eight-fold auxotrophic strain and two ultraviolet-sensitive derivatives. Mutat. Res. 15:1–10.
11. Weisblum, B., M. Y. Graham, and D. Dubnau. 1979. Plasmid copy number control: isolation and characterization of high-copy-number mutants of plasmid pE194. J. Bacteriol. 137:635–643.
12. Hohn, B. 1979. In vitro packaging of lambda and cosmid DNA. Methods Enzymol. 68:299–309.
13. Rottlander, E., and T. A. Trautner. 1970. Genetic and transfection studies with *Bacillus subtilis* phage SP50. Mol. Gen. Genet. 108:47–60.
14. Terzaghi, B. E., and W. E. Sandine. 1975. Improved medium for lactic streptococci and their bacteriophages. Appl. Microbiol. 29:807–813.
15. de Vos, W. M., G. Venema, U. Canosi, and T. A. Trautner. 1981. Plasmid transformation in *Bacillus subtilis*: fate of plasmid DNA. Mol. Genet. 181:424–433.
16. Ish-Horowicz, D., and J. F. Burke. 1981. Rapid and efficient cosmid cloning. Nucleic Acids Res. 9:2989–2999.
17. Chang, S., and S. N. Cohen. 1979. High frequency transformation of *Bacillus subtilis* protoplasts by plasmid DNA. Mol. Gen. Genet. 168:111–115.
18. Mandel, M., and A. Higa. 1970. Calcium-dependent bacteriophage DNA infection. J. Mol. Biol. 53:159–162.
19. Kondo, J. K., and L. L. McKay. 1982. Transformation of *Streptococcus lactis* protoplasts by plasmid DNA. Appl. Environ. Microbiol. 43:1213–1215.
20. Spizizen, J. 1958. Transformation of biochemically deficient strains of *Bacillus subtilis* by deoxynucleate. Proc. Natl. Acad. Sci. USA 44:1072–1078.
21. Adams, M. N. 1959. Bacteriophages. Interscience Publishers, New York.
22. Scheer-Abramowitz, J., F. J. Gryczan, and D. Dabnau. 1981. Origin and mode of replication of plasmids pE194 and pUB110. Plasmid 6:67–77.
23. Southern, E. M. 1975. Detection of specific sequences among DNA fragments separated by gel electrophoresis. J. Mol. Biol. 98:503–517.
24. Barany, F., J. D. Boeke, and A. Tomasz. 1982. Staphylococcal plasmids that replicate and express erythromycin resistance in both *Streptococcus pneumoniae* and *Escherichia coli*. Proc. Natl. Acad. U.S.A. 79:2991–2995.
25. Goze, A., and S. D. Ehrlich. 1980. Replication of plasmids from *Staphylococcus aureus* in *Escherichia coli*. Proc. Natl. Acad. Sci. U.S.A. 77:7333–7337.
26. Jarvis, A. W., and B. D. W. Jarvis. 1981. Deoxyribonucleic acid homology among lactic streptococci. Appl. Environ. Microbiol. 41:77–83.
27. Klotz, L. C., and B. H. Zimm. 1972. Size of DNA by viscoelastic measurements: results on bacteriophages. *Bacillus subtilis* and *Escherichia coli*. J. Mol. Biol. 72:779–800.
28. Ostroff, G. R., and J. J. Pène. 1983. Molecular cloning with bifunctional plasmid vectors in *B. subtilis*: Isolation of a spontaneous mutant of *B. subtilis* with enlarged transformability for *E. coli*-propagated chimeric plasmid DNA. J. Bacteriol. 156:934–936.
29. Exterkate, F. A. 1975. An introductory study of the proteolytic system of *S. cremoris* strain HP. Neth. Milk Dairy J. 29:303–318.
30. Covarrubias, L., and F. Bolivar. 1982. Construction and characterisation of new cloning vehicles VI. Plasmid pBR329, a new derivative of pBR328 lacking the 482-base-pair inverted duplication. Gene 17:79–89.
31. Chang, A. C. Y., and S. N. Cohen. 1978. Construction and characterization of amplifiable multicopy DNA cloning vehicles derived from the P15A cryptic miniplasmid. J. Bacteriol. 134:1141–1156.

32. Limsowtin, G. K. Y., and B. E. Terzaghi. 1976. Agar medium for the differentiation of "fast" and "slow" coagulating cells in lactic streptococcal cultures. N. Z. J. Dairy Sci. Technol. 11:65–66.

32a. Brown, J. Howard and Howe, Paul E., 1922. Transparent Milk as a Bacteriological Medium. J. Bacteriol. 7:511–514.

33. LeBlanc, D. J., and L. N. Lee. 1979. Rapid screening procedure for detection of plasmids in streptococci. J. Bacteriol. 140: 1112–1115.

34. Blin, N., A. V. Gabain, and H. Bujard. 1975. Isolation of large molecular weight DNA from agarose gels for further digestion by restriction enzymes. FEBS Lett. 53:84–86.

35. Okamoto, T., Y. Fujita, and R. Irie. 1983. Protoplast formation and regeneration of S. lactis cells. Agric. Biol. Chem. 47:259–263.

36. Bradford, M. M. 1976. A rapid and sensitive method for the quantitation of microgram quantities of protein utilizing the principle of protein-dye binding. Anal. Biochem. 72:248–254.

37. Elferink, M. G., K. J. Hellingwerf, P. A. Michels, H. G. Seyen, and W. N. Konings. 1979. Immunochemical analysis of membrane vesicles and chromatophores of Rhodopseudomonas sphaeroides by crossed immunoelectrophoresis. FEBS Lett. 107:300–307.

38. Norrander, J., T. Kempe, and J. Messing. 1983. Construction of improved M13 vectors using oligodeoxynucleotide-directed mutagenesis. Gene 26:101–106.

39. Towbin, H., T. Staehlin and J. Gordon. 1979. Electrophoretic transfer of proteins from polyacrylamide gels to nitrocellulose sheets: Procedure and some applications. Proc. Nat. Acad. Sci. U.S.A. 76, 4350–4354.

40. Exterkate, F. A. 1976. Comparison of strains of S. cremoris for proteolytic activities associated with the cell wall. Neth. Milk Dairy J. 30:95–105.

41. Larsen, L. D., and L. L. McKay. 1978. Isolation and characterisation of plasmid DNA in S. cremoris. Appl. Environ. Microbiol. 36:944–952.

42. Rigby, P. W. J., M. M. Dieckmann, C. Rhodes, and P. Berg. 1977. Labeling DNA to high specific activity in vitro by nick translation with DNA polymerase I. J. Mol. Biol. 113:237–251.

We claim:

1. A recombinant plasmid capable of replication in each of the microorganisms Bacillus subtilis, Escherichia coli and lactic acid streptococcus bacteria, comprising (i) at least the part of the *streptococcus cremoris* plasmid pWV01 which carries the replication origin for expression in *streptococcus cremoris*, (ii) at least one coding marker capable of expression in said microorganisms, and (iii) at least one piece of insert-DNA expressible in said microorganisms to give said microorganism improved fermenting properties.

2. The recombinant plasmid as claimed in claim 1, which comprises at least two coding markers capable of expression in the three types of said microorganisms, said markers being genes selected from the group consisting of antibiotic-resistant and auxotrophic genes.

3. The recombinant plasmid as claimed in claim 1, which comprises at least one coding marker capable of being inactivated by the insertion of insert-DNA.

4. The recombinant plasmid as claimed in claim 3, comprising the coding markers $Cm^R$ and $Em^R$.

5. The recombinant plasmid as claimed in claim 1, comprising plasmid pGKV500, obtainable by inserting the 4.3 Md HindIII fragment C of the *Streptococcus cremoris* Wg2 plasmid pWV05 into the unique HindIII site of plasmid pGKV2.

6. The recombinant plasmid as claimed in claim 1, comprising at least one auxotrophic coding marker.

7. The recombinant plasmid as claimed in claim 6, in which said auxotrophic marker is a gene encoding an enzyme involved in the metabolism of lactose.

8. The recombinant plasmid as claimed in claim 7, in which said gene originates from the BclI fragment of plasmid pLP712.

9. A lactic acid bacterium of the genus streptococcus comprising the recombinant plasmid as claimed in claim 1, the insert-DNA being a gene encoding protease, a gene encoding a milk-clotting enzyme, a gene providing bacteriophage resistance or a gene involved in citrate or lactose metabolism.

10. The Streptococcus bacterium according to claim 9, which is selected from the group consisting of *Streptococcus cremoris*, *Streptococcus diacetilactis* and *Streptococcus lactis*.

* * * * *